(12) United States Patent
Smythe et al.

(10) Patent No.: US 10,208,591 B2
(45) Date of Patent: Feb. 19, 2019

(54) FLUSHING MICROFLUIDIC SENSOR SYSTEMS

(71) Applicant: SCHLUMBERGER TECHNOLOGY CORPORATION, Sugar Land, TX (US)

(72) Inventors: Elizabeth Jennings Smythe, Cambridge, MA (US); Christopher Harrison, Auburndale, MA (US); John Meier, Boston, MA (US); Matthew Sullivan, Westwood, MA (US); Shunsuke Fukagawa, Arlington, MA (US)

(73) Assignee: SCHLUMBERGER TECHNOLOGY CORPORATION, Sugar Land, TX (US)

( * ) Notice: Subject to any disclaimer, the term of this patent is extended or adjusted under 35 U.S.C. 154(b) by 95 days.

(21) Appl. No.: 14/977,018

(22) Filed: Dec. 21, 2015

(65) Prior Publication Data
US 2017/0175522 A1  Jun. 22, 2017

(51) Int. Cl.
| | |
|---|---|
| *E21B 49/08* | (2006.01) |
| *B01L 3/00* | (2006.01) |
| *G01N 9/00* | (2006.01) |
| *G01N 11/16* | (2006.01) |
| *E21B 49/10* | (2006.01) |

(52) U.S. Cl.
CPC ........ *E21B 49/08* (2013.01); *B01L 3/502738* (2013.01); *E21B 49/10* (2013.01); *G01N 9/002* (2013.01); *G01N 11/16* (2013.01); *B01L 2200/146* (2013.01); *B01L 2300/0663* (2013.01); *B01L 2300/14* (2013.01); *B01L 2300/165* (2013.01); *B01L 2400/0478* (2013.01); *B01L 2400/0605* (2013.01); *B01L 2400/0616* (2013.01); *G01N 2009/006* (2013.01)

(58) Field of Classification Search
CPC ........................................................ E21B 49/08
USPC ........................................... 73/152.23, 54.41
See application file for complete search history.

(56) References Cited

U.S. PATENT DOCUMENTS

| | | | |
|---|---|---|---|
| 4,994,671 A | 2/1991 | Safinya et al. | |
| 5,269,180 A * | 12/1993 | Dave | E21B 33/1246 166/250.02 |

(Continued)

FOREIGN PATENT DOCUMENTS

| | | | | |
|---|---|---|---|---|
| WO | WO 2009052235 A1 * | 4/2009 | | E21B 49/10 |
| WO | WO 2014158376 A1 * | 10/2014 | | E21B 47/06 |

OTHER PUBLICATIONS

WO2009052235.*

(Continued)

*Primary Examiner* — Manish S Shah
*Assistant Examiner* — Jean Morello

(57) ABSTRACT

A method and an apparatus for characterizing a fluid provide for flowing a sample fluid through a microfluidic flow line in a first direction and into contact with a microfluidic sensor, measuring a property of the fluid sample using the microfluidic sensor; and after measuring the property of the fluid sample, flushing the microfluidic sensor by flowing a solvent through the microfluidic flow line in a second direction that is opposite the first direction.

41 Claims, 12 Drawing Sheets

(56) References Cited

U.S. PATENT DOCUMENTS

| | | | |
|---|---|---|---|
| 6,501,072 B2* | 12/2002 | Mullins | E21B 47/102 |
| | | | 250/255 |
| 7,384,453 B2 | 6/2008 | Bostrom et al. | |
| 7,575,681 B2 | 8/2009 | Angelescu et al. | |
| 7,637,151 B2 | 12/2009 | Raghuraman et al. | |
| 7,677,307 B2* | 3/2010 | Vasques | E21B 37/00 |
| | | | 166/250.01 |
| 8,028,562 B2 | 10/2011 | Shah et al. | |
| 8,262,909 B2 | 9/2012 | Angelescu et al. | |
| 8,910,514 B2 | 12/2014 | Sullivan et al. | |
| 9,638,681 B2 | 5/2017 | Zhdaneev et al. | |
| 2010/0265492 A1 | 10/2010 | Schroeder et al. | |
| 2010/0268469 A1 | 10/2010 | Harrison et al. | |
| 2013/0186185 A1 | 7/2013 | Harrison et al. | |
| 2013/0219997 A1 | 8/2013 | Sullivan et al. | |
| 2014/0221256 A1* | 8/2014 | Holtsclaw | C08L 33/14 |
| | | | 507/211 |
| 2014/0260586 A1* | 9/2014 | Van Hal | E21B 49/082 |
| | | | 73/152.07 |
| 2014/0268156 A1 | 9/2014 | Smythe et al. | |
| 2015/0007631 A1 | 1/2015 | Pelletier et al. | |
| 2015/0007974 A1* | 1/2015 | Parsche | E21B 36/04 |
| | | | 166/57 |
| 2015/0021097 A1* | 1/2015 | Wesemeier | E21B 25/00 |
| | | | 175/59 |

OTHER PUBLICATIONS

WO2014/158376.*
International search report and written opinion for WO2017/112429.*

* cited by examiner

FLUSHING MICROFLUIDIC SENSOR SYSTEMS

BACKGROUND

The oil and gas industry has developed various tools capable of determining formation fluid properties. For example, borehole fluid sampling and testing tools such as Schlumberger's Modular Formation Dynamics Testing (MDT) Tool can provide important information on the type and properties of reservoir fluids in addition to providing measurements of reservoir pressure, permeability, and mobility. These tools may perform measurements of the fluid properties downhole, using sensor modules on board the tools. These tools can also withdraw fluid samples from the reservoir that can be collected in bottles and brought to the surface for analysis. The collected samples are routinely sent to fluid properties laboratories for analysis of physical properties that include, among other things, oil viscosity, gas-oil ratio, mass density or API gravity, molecular composition, $H_2S$, asphaltenes, resins, and various other impurity concentrations.

The reservoir fluid may break phase in the reservoir itself during production. For example, one zone of the reservoir may contain oil with dissolved gas. During production, the reservoir pressure may drop to the extent that the bubble point pressure is reached, allowing gas to emerge from the oil, causing production concerns. Knowledge of this bubble point pressure may be helpful when designing production strategies Characterizing a fluid in a laboratory utilizes an arsenal of devices, procedures, trained personnel, and laboratory space. Successfully characterizing a fluid in a wellbore uses methods, apparatus, and systems configured to perform similarly with less space and personal attention and to survive in conditions that quickly destroy traditional lab equipment. Identifying the undesired phase change properties of a fluid is especially useful when managing a hydrocarbon reservoir.

SUMMARY

In accordance with some example embodiments, an apparatus for measuring a property of a fluid sample includes: a microfluidic flow line; an inlet valve fluidically coupled to a first end of the microfluidic flow line and configured to allow the fluid sample to flow from an inlet line into the microfluidic flow line when the inlet valve is in an open state; an outlet valve fluidically coupled to a second end of the microfluidic flow line opposite the first end of the microfluidic flow line and configured to allow the fluid sample to flow out of the microfluidic flow line and into an outlet line when the outlet valve is in an open state; a piston configured to control fluid pressure in the microfluidic flow line; a microfluidic sensor configured to measure the property of the fluid sample, the microfluidic sensor being disposed along the microfluidic flow line at a location between the inlet valve and a location at which the piston fluidically interfaces the microfluidic line; and a solvent reservoir configured to deliver a solvent into the microfluidic flow line, wherein the apparatus is configured to move the solvent through the microfluidic sensor in a direction toward the inlet valve.

In accordance with some example embodiments, a method includes: flowing a sample fluid through a microfluidic flow line in a first direction and into contact with a microfluidic sensor; measuring a property of the fluid sample using the microfluidic sensor; and after measuring the property of the fluid sample, flushing the microfluidic sensor by flowing a solvent through the microfluidic flow line in a second direction that is opposite the first direction.

Further features and aspects of example embodiments of the present invention are described in more detail below with reference to the appended Figures.

FIGURES

DESCRIPTION

Figure 1:
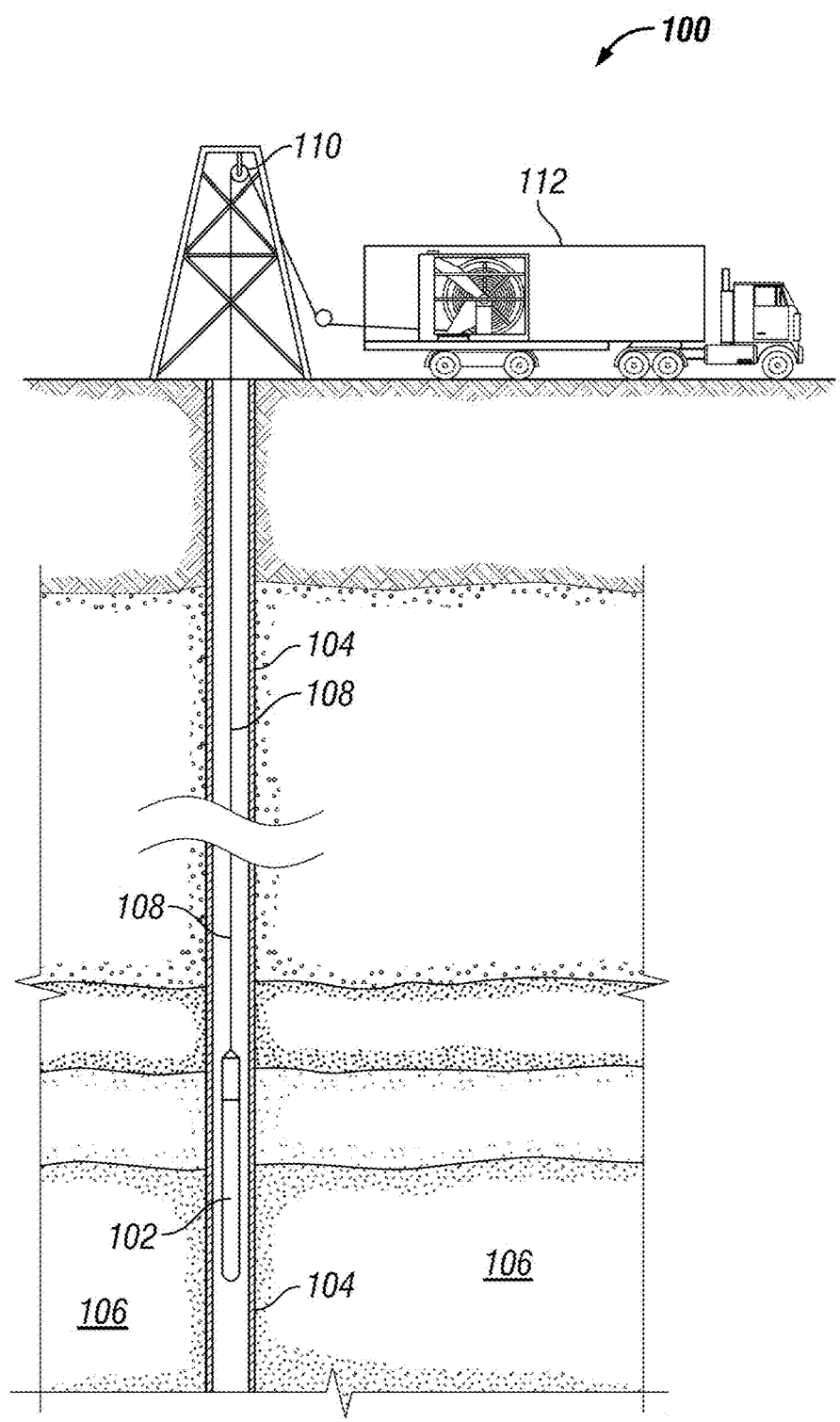
FIG. 1 is a schematic of a drilling system according to example embodiments.

Example embodiments disclosed herein provide methods, apparatuses, and systems for measuring the temperature dependence of several fluid properties, including but not limited to, density, viscosity, and the bubble point. A fluid analysis device, e.g., a pressure-volume-temperature (PVT) apparatus, may be deployed in a downhole tool that could operate in an open or cased hole environment during a sampling job, but the fluid analysis device may also have applicability for production logging and surface applications. For downhole applications, the temperature of the fluid analysis device can be controlled to bring the sampled fluid to those temperatures that the fluid would be subjected to during production as the fluid was transported from reservoir to the surface.

Some examples include mechanisms to address build-up and contamination of sensors and/or membranes in a downhole environment.

Some examples include mechanisms to clean or flush sensors and/membranes using, alone or in combination: Pulsed electric or magnetic fields, chemical solutions, and microwave/ultrasonic heating.

One difficulty in making accurate measurements with a fluid sensor is the challenge of completely flushing away the first fluid under measurement when switching to a second fluid to be measured. A practice for eliminating cross-contamination between fluids is to vigorously flush the sensor, and other relevant surfaces and flowlines, with an appropriate solvent. The volume of fluid utilized to flush sensors when the sensors are of standard size and are installed in downhole tools that involve long flowlines can be so large that flushing becomes impractical. In contrast, microfluidic sensors are of low volume, and when installed in an appropriate environment, require correspondingly low volumes to flush clean, rendering them more practically "flushable," even for the most extreme unfavorable viscosity ratios. Examples described herein provide for flushing of microsensors, micro flowlines, and a filtering membrane so as to facilitate an accurate measurement with a practical volume of fluid in an acceptable amount of time.

Perhaps the best example of the flushing problem would be that of a wireline tool that performs Downhole Fluid Analysis (DFA) and firstly samples from a crude (black) oil zone, followed by sampling from a gas zone (or retrograde condensate). The flow of gas through a wireline tool is generally inadequate to displace crude oil to the extent that sensors often read a biased or inaccurate example. For example, even after pumping gas for a long time, there are often traces of oil on the sapphire spectrometer windows, biasing the measurement. As well, the density measurement components tend to be biased when trying to measure gas properties after an oil sampling job. For certain jobs, sample bottles have been pre-filled with solvents to help flush downhole sensors, but results are not particularly satisfying, and wind up adding a large amount of length to the toolstring.

Figure 7A:
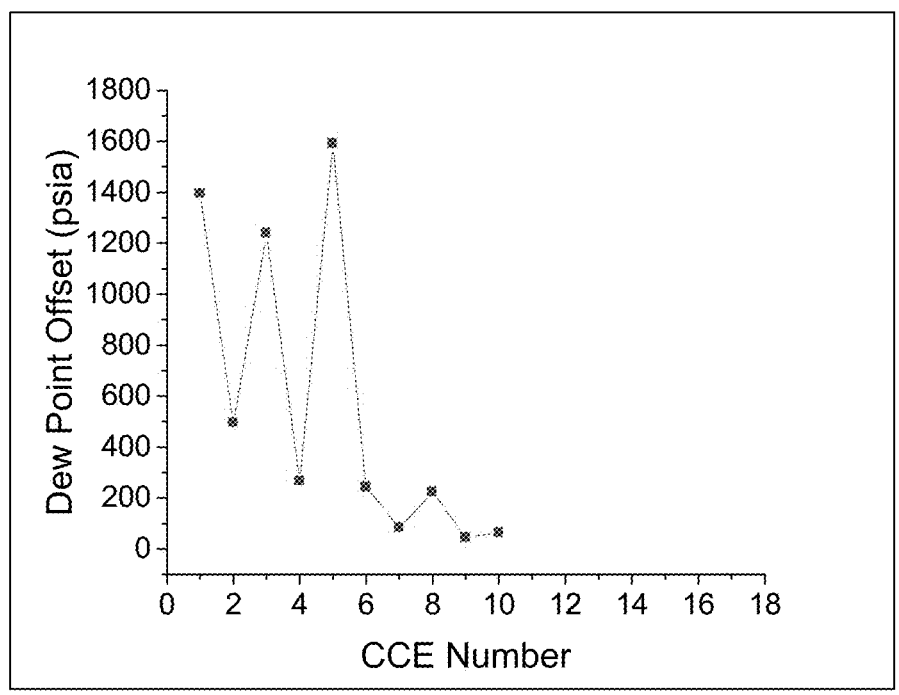
FIG. 7A shows a graph of dew point offset and CCE number for systems that do not include the solvent flushing of example embodiments of the present invention.

FIG. 7A presents data from a microfluidic phase transition cell as an example of the challenge encountered when trying to measure a dewpoint in a microfluidic system after first filling up the microfluidic system with a crude oil. Retrograde condensate gases at pressures above their dewpoints act as typical vapors or gases and are of very low viscosity, typically 0.1 cP or significantly less. As such, trying to displace a crude oil with viscosity of order 1 cP or greater with a retrograde condensate gas would present a very unfavorable viscosity ratio, which is known to create a flushing challenge. Hence, it is found that a large volume of retrograde condensate gas needs to be flushed through the system to fully remove the crude oil, and many CCEs (Constant Composition Expansion, part of a dewpoint measurement involving sample isolation and pressure decrease). As a further difficulty, crude oils are minimally soluble in retrograde condensate gases, meaning that traces of crude oil can be left behind in a microfluidic system when flushing with retrograde condensate gases, biasing the any measurements made on them, such as dewpoint pressure Pd, viscosity, density, compressibility, etc.

Referring to FIG. 7A, for each dewpoint measurement, a CCE is performed, requiring a volume of retrograde gas condensate to be flushed through the system, followed by the condensate being isolated and depressurized. The early dewpoint measurements show a large degree of scatter and 36 minutes are required to perform the 10 CCEs shown. Nonlimiting example solvent reservoir flushing apparatuses and methods described herein help to minimize the number of CCEs needed to reach a stable value by flushing most of the crude oil out of the system before charging it with the retrograde gas.

Tests have been performed using a structure corresponding to the schematic drawing of FIG. 3A, which is described in greater detail below. For testing, which generated the data shown in FIG. 7B, 13 cc of xylene was used to flush out crude oil from the microfluidic lines at a rate of 1.2 cc/minute. Retrograde gas condensate was then filled into the system, thereby displacing the xylene. This flushing dramatically helped to reduce the number of CCEs necessary to effect before reaching a stable dewpoint pressure.

The above-mentioned 13 cc of solvent is an extraordinarily small volume of liquid compared to the multiple liters of solvent need to clean out the main flow line of a typical oilfield sampling tool (such main flow line would correspond to flow line 204 in the illustrated examples).

Figure 7B:
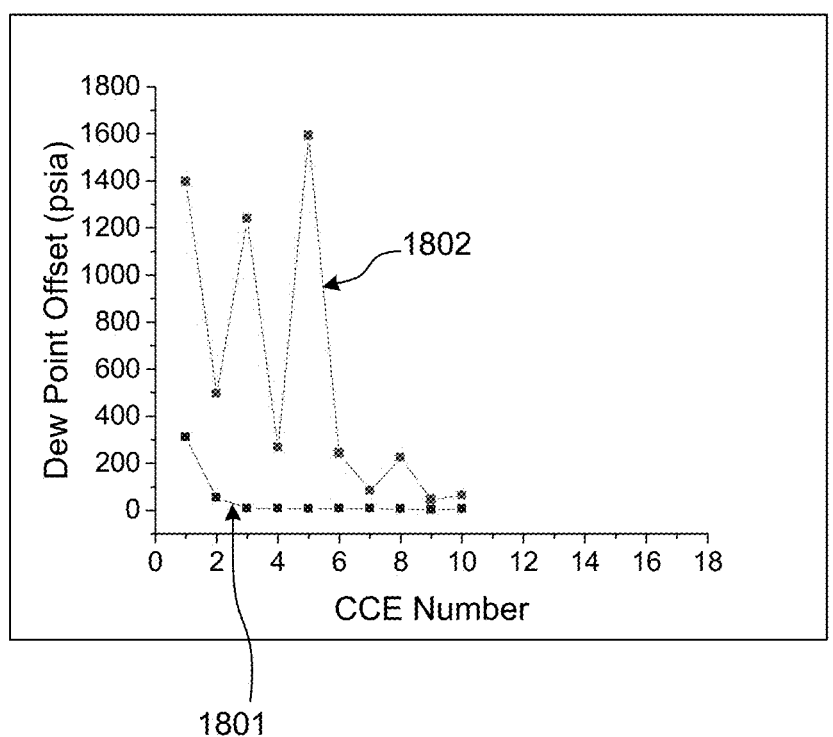
FIG. 7B shows the data of FIG. 7A superimposed on a graph of dew point offset and CCE number for a system that corresponds to the apparatus of FIG. 3A.

Referring to FIG. 7B, the lower data line 1801 shows that a stable dewpoint measurement can be achieved when using xylene or toluene flushing (which are non-limiting examples) with a solvent reservoir within a few CCEs. The upper data line 1802 corresponds to the data shown in FIG. 7A and is included as a comparison and shows the difficulty in reaching a stable dewpoint when solvent flushing of the system is not possible.

FIG. 1 shows one example of a wireline logging system 100 at a well site. Such a wireline logging system 100 can be used to implement a rapid formation fluid analysis. In this example, a wireline tool 102 is lowered into a wellbore 104 that traverses a formation 106 using a cable 108 and a winch 110. The wireline tool 102 is lowered down into the wellbore 104 and makes a number of measurements of the adjacent formation 106 at a plurality of sampling locations along the wellbore 104. The data from these measurements is communicated through the cable 108 to surface equipment 112, which may include a processing system for storing and processing the data obtained by the wireline tool 102. The surface equipment 112 includes a truck that supports the wireline tool 102. In other embodiments, the surface equipment may be located in other locations, such as within a cabin on an off-shore platform.

Figure 2:
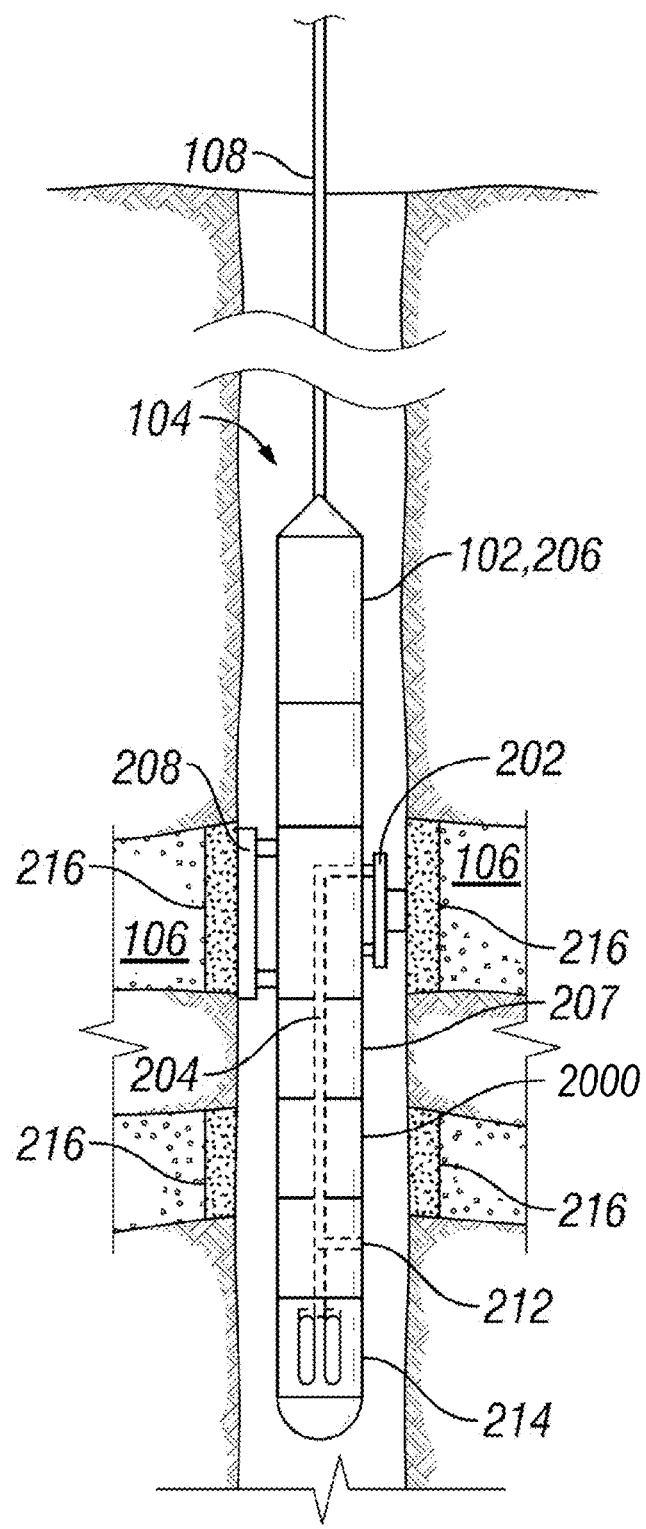
FIG. 2 is a flow chart of one embodiment of a process according to embodiments herein.

FIG. 2 shows a more detailed view of the wireline tool 102. The wireline tool 102 includes a selectively extendable fluid admitting assembly (e.g., probe) 202. This assembly 202 extends into the formation 106 and withdraws formation fluid from the formation 116 (e.g., samples the formation). The fluid flows through the assembly 202 and into a main flow line 204 within a housing 206 of the tool 102. A pump module 207 is used to withdraw the formation fluid from the formation 106 and pass the fluid through the flow line 204. The wireline tool 102 may include a selectively extendable tool anchoring member 208 that is arranged to press the probe 202 assembly against the formation 106.

The wireline tool 102 also includes a fluid analysis system 2000 for analyzing at least a portion of the fluid in the flow line 204.

After the fluid analysis system 2000, the formation fluid may be pumped out of the flow line 204 and into the wellbore 104 through a port 212. Some of the formation fluid may also be passed to a fluid collection module 214 that includes chambers for collecting fluid samples and retaining samples of the formation fluid for subsequent transport and testing at the surface (e.g., at a testing facility or laboratory).

Figure 3A:
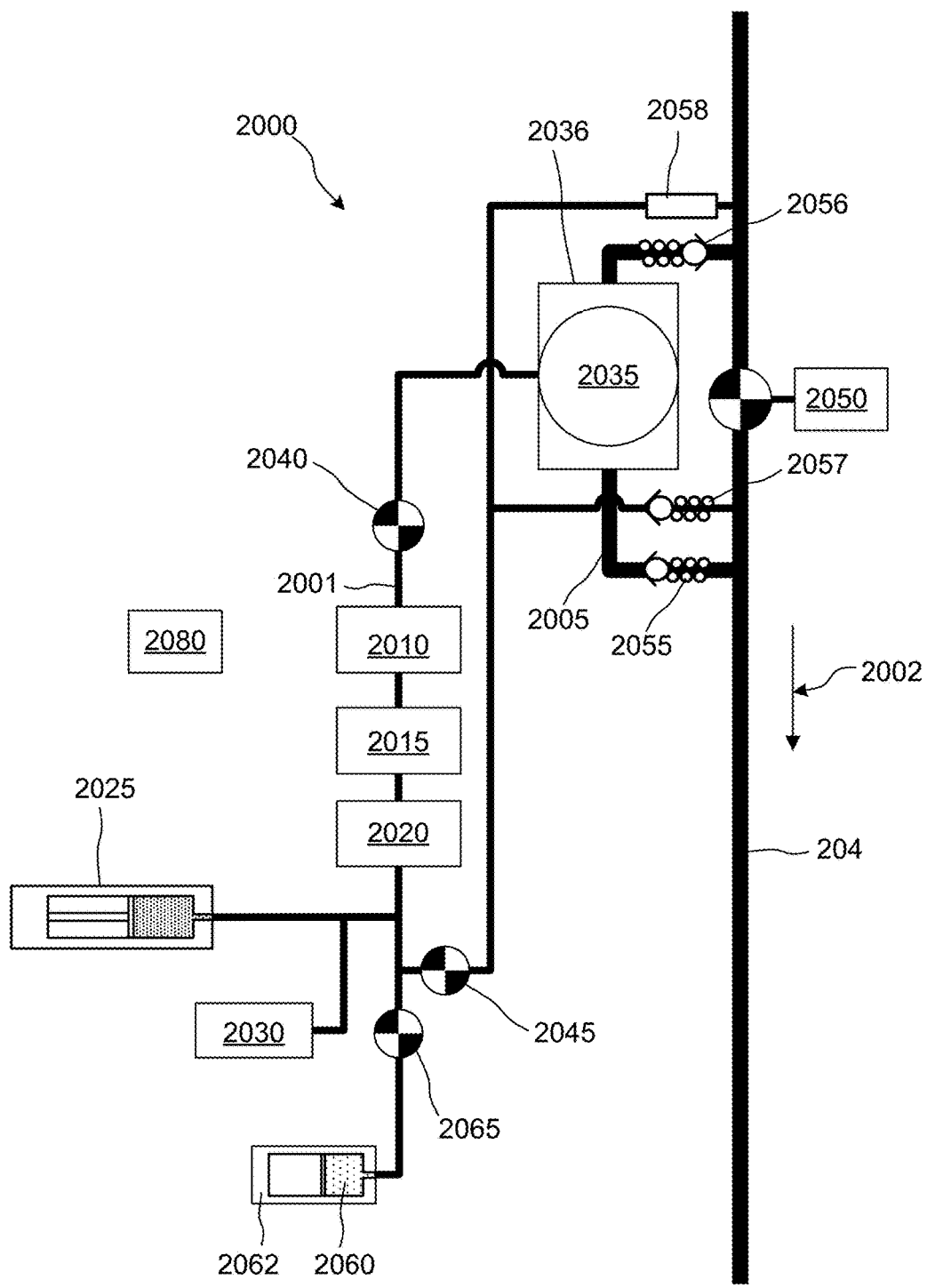
FIG. 3A is a schematic drawing of a fluid analysis system according example embodiments.

FIG. 3A shows a more detailed view of a fluid analysis system 2000. As shown in FIG. 3A, the fluid analysis system 2000 includes a bypass flow line 2005 that is coupled to the main flow line 204. The bypass flow line 2005 also includes a membrane 2035 to separate water from the formation fluid sample (e.g., a hydrophobic membrane). Such a membrane is described in U.S. Pat. No. 7,575,681 issued on Aug. 18, 2009 and U.S. Pat. No. 8,262,909 issued on Sep. 11, 2012, each of which is hereby incorporated by reference in its entirety.

In some embodiments, a pump or a piston is used to extract the formation fluid sample from the main flow line 204 and pass the formation fluid through the membrane 2035. In various embodiments, the membrane 2035 separates water from the formation fluid sample as the sample passes from the bypass flow line 2005 into a microfluidic secondary flow line 2001 for fluid analysis. Although a single membrane 2035 is provided in the illustrated examples, it should be understood that some embodiments include multiple membranes.

Once the formation fluid sample passes the membrane 2035, the sample flows into the microfluidic secondary flow line 2001 to fluid analysis modules (e.g., phase transition cell 2010, densitometer 2015, and viscometer 2020, described in further detail below and illustrated in, for example, FIG. 3A) that analyze the sample to determine at least one property of the fluid sample. In some examples, the fluid analysis modules are in electronic communication with the surface equipment 112 through, for example, a telemetry module and the cable 108. Accordingly, in some examples, the data produced by the fluid analysis modules can be communicated to the surface for further processing by a processing system.

In addition or as an alternative to the phase transition cell 2010, densitometer 2015, and viscometer 2020 mentioned above, the fluid analysis modules can include a number of different devices and systems that analyze the formation fluid sample. For example, in some examples, the fluid analysis modules include a spectrometer that uses light to determine a composition of the formation fluid sample. The spectrometer can determine an individual fraction of methane ($C_1$), an individual fraction of ethane ($C_2$), a lumped fraction of alkanes with carbon numbers of three, four, and five ($C_3$-$C_5$), and a lumped fraction of alkanes with a carbon number equal to or greater than six ($C_{6+}$). An example of such a spectrometer is described in U.S. Pat. No. 4,994,671 issued on Feb. 19, 1991 and U.S. Patent Application Publication No. 2010/0265492 published on Oct. 21, 2012, each of which is incorporated herein by reference in its entirety. In some embodiments, the fluid analysis modules include a gas chromatograph that determines a composition of the formation fluid. In some embodiments, the gas chromatograph determines an individual fraction for each alkane within a range of carbon numbers from one to 25 ($C_1$-$C_{25}$). Examples of such gas chromatographs are described in U.S. Pat. No. 8,028,562 issued on Oct. 4, 2011 and U.S. Pat. No. 7,384,453 issued on Jun. 10, 2008, each of which is hereby incorporated by reference in its entirety. The fluid analysis module may include a mass spectrometer, a visible absorption spectrometer, an infrared absorption spectrometer, a fluorescence spectrometer, a resistivity sensor, a pressure sensor, and/or a temperature sensor. The fluid analysis modules may include combinations of such devices and systems. For example, the fluid analysis modules may include a spectrometer followed by a gas chromatograph as described in, for example, U.S. Pat. No. 7,637,151 issued on Dec. 29, 2009 and U.S. patent application Ser. No. 13/249,535 filed on Sep. 30, 2011, each of which is incorporated herein by reference in its entirety. Although examples may provide multiple fluid analysis modules, it should be understood that some examples provide only a single fluid analysis module.

In the example of FIG. 3A, the fluid analysis system 2000 includes a phase transition cell 2010 followed by a densitometer 2015 and a viscometer 2020. As explained above, other combinations of devices and systems that analyze the formation fluid sample are also possible.

The fluid analysis system 2000 also includes a pressure unit 2025 for changing the pressure within the fluid sample and a pressure sensor 2030 that monitors the pressure of the fluid sample within the microfluidic secondary line 2001 at the location where the sample is to be analyzed. In some embodiments, the pressure unit 2025 is a piston that is in communication with the microfluidic line 2001 and that applies positive or negative pressure to the fluid sample to respectively increase or decrease the pressure of the sample. As explained below, the system 2000 includes valves to isolate the formation fluid sample within the analysis region of the microfluidic line 2001 as the pressure is increased or decreased. Also, in some embodiments, the pressure unit 2025 may be used to extract the formation fluid sample from the bypass flow line 2005 by changing the pressure within the secondary flow line 2001. The pressure sensor 2030 is used to monitor the pressure of the fluid sample within the secondary flow line 2001. The pressure sensor 2030 can be, for example, a strain gauge or a resonating pressure gauge. By changing the pressure of the fluid sample, the fluid analyzer module 210 can make measurements related to phase transitions of the fluid sample (e.g., bubble point or asphaltene onset pressure measurements). Further details of devices and systems that analyze the formation fluid sample are also provided in PCT Application Publication No. WO 2014/158376 A1, which is hereby incorporated herein by reference in its entirety.

Referring to FIG. 1, near the bottom of the wellbore 104, the pressure may be sufficiently high that the fluid is single-phase. At a given mid-point (the location of which may vary depending on well properties), the pressure may reach the bubble point when the fluid breaks phase, producing gaseous and liquid phases. While the fluid is transiting from the wellbore bottom to the surface, the temperature is monotonically decreasing, increasing the fluid viscosity.

Fluids that may be produced from the formation have their temperature changed as they are brought to the surface, and hence experience a dramatic change in the fluid properties, including but not limited to their density. In order to accurately calculate the flow rate during production, an accurate knowledge of the density as a function of depth is useful. Along with temperature dependence, the fluid pressure may drop below the bubble point while in transit. Some example systems 100 may obtain a fluid sample from the formation and rapidly vary its temperature in order to simulate the fluid's passage through the oilwell during the production stage. In some embodiments, the tool 102 may store a sample extracted from the formation after measurements are performed. The tool 102 may be raised to a shallower depth and allow the sample within the device to come to equilibrium, after which additional measurements may be performed. It should be understood that although the tool 102 in the illustrated examples is a wireline tool, the features of the tool 102 may implemented into any suitable apparatus and may be provided to operate in downhole and/or surface locations.

As an example, a description for measuring density will be discussed, with a comparison of the amount of energy to change the sample temperature for both mesoscopic and microfluidic approaches. This would apply as well to a bubble point measurement where one is interested in the temperature dependence as well. The present embodiments may be compared to a conventional viscometer that is macroscopic in size and is directly immersed in the flow-line which has an inner diameter of approximately 5.5 mm. The total amount of fluid to fill the conventional sensors and the surrounding region volume is on the order of 10 milliliters, with an associated heat capacity of, assuming the specific heat of mineral oil, 1.7 Joules/(gram Kelvin), or a heat capacity of approximately 20 Joules/Kelvin. Hence, 20 Joules of energy are removed to reduce the temperature by one degree Kelvin. Furthermore, as the sensors are thermally connected to a large metallic assembly on the order of 1 kilogram (or more), in practice one would reduce the temperature of this assembly as well. Assuming a specific heat of 0.5 Joules/(gram Kelvin) for steel, one would have to remove 500 Joules of energy to reduce the temperature of the whole assembly by one degree. This approach using conventional technologies will be referred to as mesoscopic herein.

As a comparison, microfluidic environments of the present disclosure may use fluid volumes on the order of ten microliters, which corresponds to around 10 milligrams of liquid, which has a heat capacity of about 0.02 Joules/Kelvin (using the above numbers for the specific heat). In practice, one controls the temperature of the microfluidic chamber as well, which may have a mass on the order of 50 grams, and assuming this is fabricated from titanium, with a specific heat of 0.5 Joules/(gram Kelvin), it would use on the order of 25 Joules of energy to change the temperature by one degree. Note that this power usage for the microfluidic approach is 20 times smaller than for mesoscopic approach. Peltier (or thermoelectric) coolers reveals that models with dimensions with the proper scale exist and are specified to produce heat fluxes on the order of 1 Joule/second (1 watt), and one may quickly ramp up or down the temperature of such a device. Hence, a rapid ramping up or down of the temperature of a microfluidic-scale of fluidic volume and associated chamber is feasible.

As indicated above, during a process of sampling fluid into the fluid analysis system 2000, a fluid may be sampled from the formation 106. In some embodiments, a small volume (on the order of tens of microliters) of fluid will be sampled, filtered, and passed into the microfluidic line 2001 of the analysis system 2000. In some examples, the system 2000 may be placed into a pressure compensation system where during the initial phase of its operation, the pressure in microfluidic line 2001 is approximately 100 psi lower (or less) than the flow line 204 of the tool in which it will be implemented. As discussed above, the microfluidic fluid analysis system 2000 may include microfluidic sensors to measure the density, viscosity and/or any other physical properties of the fluid. The microfluidic system 2000 may either be located downhole or at the surface.

For some example downhole applications, the fluid evaluation may be motivated by the fact that wellbore temperature changes substantially from the formation to the surface. Fluids that are produced from the formation change their temperature accordingly and hence experience a dramatic change in their properties, including but not limited to their density. In order to accurately calculate the flow rate during production one should accurately know the density as a function of depth. This is further complicated by the fact that the fluid may drop below the bubble point while in transit. Hence, a system may be selected that can obtain a fluid sample from the formation and rapidly vary its temperature in order to simulate its passage through the wellbore during the production stage.

Generally, examples disclosed herein relate to collecting a fluid from a wellbore, a fracture in a formation, a body of water or oil or mixture of materials, or other void in a subterranean formation that is large enough from which to collect a sample. The fluid may contain solid particles such as sand, salt crystals, proppant, solid acids, solid or viscous hydrocarbon, viscosity modifiers, weighing agents, completions residue, or drilling debris. The fluid may contain water, salt water, hydrocarbons, drilling mud, emulsions, fracturing fluid, viscosifiers, surfactants, acids, bases, or dissolved gases such as natural gas, carbon dioxide, or nitrogen.

Systems for analyzing these fluids may be located in various locations or environments, including, but not limited to, tools for downhole use, permanent downhole installations, or any surface system that will undergo some combination of elevated pressures, temperatures, and/or shock and vibration. In some embodiments, temperatures may be as high as about 175° C. or about 250° C. with pressures as high as about 25,000 psi.

In general, energy added to a fluid at pressures near the bubble point to overcome the nucleation barrier associated with bubble production. Thus, energy may be added to a fluid thermally through the process of thermal nucleation. The quantity of bubbles produced at the thermodynamic bubble point via thermal nucleation is sufficiently small that their presence is detectable near the place of thermal nucleation in a phase transition cell and not in other components in the measurement system. However, upon further depressurization of the system, the supersaturation becomes large enough that bubble nucleation spontaneously occurs throughout the measurement system. In one or more embodiments, a fluid sample may be depressurized at a rate such that bubble detection may occur in a phase transition cell alone, or may be sufficiently high enough to be detected throughout the overall system.

During depressurization of a sample, the density, viscosity, optical transmission through the phase transition cell, and sample pressure may be simultaneously measured. Depressurization starts at a pressure above the saturation pressure and takes place with a constant change in system volume, a constant change in system pressure, or discreet pressure changes.

Collecting and analyzing a small sample with equipment with a small interior volume allows for precise control and rigorous observation when the equipment is appropriately tailored for measurement. At elevated temperatures and pressures, the equipment may also be configured for effective operation over a wide temperature range and at high pressures. Selecting a small size for the equipment is advantageous for rugged operation because the heat transfer and pressure control dynamics of a smaller volume of fluid are easier to control then those of large volumes of liquids. That is, a system with a small exterior volume may be selected for use in a modular oil field services device for use within a wellbore. A small total interior volume can also allow cleaning and sample exchange to occur more quickly than in systems with larger volumes, larger surface areas, and larger amounts of dead spaces. Cleaning and sample exchange are processes that may influence the reliability of the fluid analysis system 2000. That is, the smaller volume uses less fluid for observation, but also can provide results that are more likely to be accurate.

The minimum production pressure of the reservoir may be determined by measuring the saturation pressure of a representative reservoir fluid sample at the reservoir temperature. In a surface measurement, the reservoir phase envelope may be obtained by measuring the saturation pressure (bubble point or dewpoint pressures) of the sample using a traditional pressure-volume-temperature (PVT) view cell over a range of temperatures. Saturation pressure can be either the bubble or dewpoint of the fluid, depending upon the fluid type. At each temperature, the pressure of a reservoir sample is lowered while the sample is agitated with a mixer. This is done in a view cell until bubbles or condensate droplets are optically observed and is known as a Constant Composition Expansion (CCE). The PVT view cell volume is on the order of tens to hundreds of milliliters, thus using a large volume of reservoir sample to be collected for analysis. This sample can be consumed or altered during PVT measurements. A similar volume may be used for each additional measurement, such as density and viscosity, in a surface laboratory. Thus, the small volume of fluid used by microfluidic sensors of the present disclosure (approximately 1 milliliter total for measurements described herein) to make measurements may be highly advantageous.

In one or more embodiments, for example, the system 2000, an optical phase transition cell 2010 may be included in a microfluidic PVT tool. It may be positioned in the fluid path line to subject the fluid to optical interrogation to determine the phase change properties and its optical properties. U.S. patent application Ser. No. 13/403,989, filed on Feb. 24, 2012 and U.S. Patent Application Publication Number 2010/0265492, published on Oct. 21, 2010 describe embodiments of a phase transition cell and its operation. Each of these applications is incorporated herein by reference in its entirety. The phase transition cell 2010 detects the dew point or bubble point phase change to identify the saturation pressure while simultaneously nucleating the minority phase.

The phase transition cell 2010 may provide thermal nucleation which facilitates an accurate saturation pressure measurement with a rapid depressurization rate of, for example, from about 10 to about 200 psi/second. As such, a saturation pressure measurement (including depressurization from reservoir pressure to saturation pressure) may take place in, for example, less than 10 minutes, as compared to the saturation pressure measurement via standard techniques in a surface laboratory, wherein the same measurement may take several hours.

Some embodiments may include a view cell to measure the reservoir asphaltene onset pressure (AOP) as well as the saturation pressures. Hence, the phase transition cell 2010 becomes a configuration to facilitate the measurement of many types of phase transitions during a CCE.

In one or more embodiments, the densitometer 2015, viscometer 2020, a pressure gauge 2030 and/or a method to control the sample pressure with a phase transition cell 2010 may be integrated so that most sensors and control elements operate simultaneously to fully characterize a live fluid's saturation pressure. In some embodiments, each individual sensor itself (e.g., densitometer 2015 or viscometer 2020) has an internal volume of no more than 20 microliters (approximately 2 drops of liquid) and by connecting each in series, the total volume (500 microliters) to charge the system with live oil before each measurement may be minimized. In some embodiments, the fluid has a total fluid volume of about 1.0 mL or less. In other embodiments, the fluid has a total fluid volume of about 0.5 mL or less.

This configuration is substantially different than a traditional PVT apparatus, but provides similar information while reducing the amount of fluid consumed for measurement.

FIG. 3A is a schematic of one embodiment of a fluid analysis system 2000 in the form of a PVT apparatus for use downhole. In some embodiments, the PVT apparatus may be included into another measurement tool or may be stand-alone on a drill string or wire line.

The system's 2000 small dead volume (e.g., less than 0.5 mL) facilitates pressure control and sample exchange. In some embodiments, the depressurization or pressurization rate of the fluid is less than 200 psi/second. In some embodiments, the fluid is circulated through the system at a volumetric rate of no more than 1 ml/sec.

Although the system 2000 of FIG. 3A includes a phase transition cell 2010 for saturation pressure detection with optical measurements, a microfluidic vibrating tube densitometer 2015 for density measurements, and a microfluidic vibrating wire viscometer 2020 for viscosity measurements, it should be understood that variations of the number and type of sensors may be provided in other examples. Compressibility measurements may also occur in some examples. The compressibility may be measured from the derivative of volume with respect to pressure with knowledge of the system 2000 volume.

As indicated above, the control of the pressure within the system 2000 may use a pressure control device 2025 in the form of a micro piston 2025. In such an embodiment, the control of the pressure in the system, in particular, the relevant portions of microfluidic secondary line 2001, may be adjusted by moving the piston to change the volume inside the piston housing and, thus, the sample volume. The system's small dead volume (less than 0.5 mL in some examples) facilitates pressure control and sample exchange. In some examples, the depressurization or pressurization rate of the fluid is less than 200 psi/second. In some embodiments, the fluid is circulated through the system at a volumetric rate of no more than 1 ml/sec.

The sample fluid is in pressure communication with the pressure gauge 2030. The pressure gauge 2030 may measure small pressure changes such as, for example, 2 to 3 psig. The gauge 2030 utilizes small sample volume for its external housing and also has low dead volume of less than about 1 mL. Some examples may have a dead volume of less than 0.5 mL or less than 0.05 mL. In some examples, the pressure gauge 2030 is a micro SOI (silicon on insulator) piezoresistive sensor, although any suitable pressure gauge may be provided.

The phase transition cell 2010 includes a flow line constrained by two sapphire windows or lenses. U.S. Patent Application Publication No. 2010/0265492 provides additional details of this arrangement and is incorporated by reference herein in its entirety. Light in the optical path between the two windows or lenses is highly sensitive to the presence of fluid interfaces, such as that associated with bubbles in a liquid (produced at bubble point) or liquid droplets in a gas (produced at dew point). An 80 percent Nickel, 20 percent Chromium (NICHROME80™) wire of diameter 100 microns or less is installed orthogonal to the flow path in the phase transition cell to thermally agitate the fluid to overcome the nucleation barrier. Some embodiments may use a wire comprising platinum, tungsten, iridium or a platinum-iridium alloy. A high current pulse (c.a. 5 amperes) of duration 5 microseconds quickly heats the fluid surrounding the wire by about 25° C. As the heat dissipates (in about 0.1 s) and the local temperature returns to that of the system, the bubbles formed in a liquid sample either collapse or remain stable, according to whether the system is above the saturation pressure or, inside the two-phase region, respectively. The mechanisms of the nucleation process and its operability on both sides of the cricondenbar are described in U.S. Patent Application Publication No. 2013/0219997 and U.S. Patent Application Publication No. 2014/0268156. Both of these references are incorporated by reference herein in their entireties.

As mentioned above, the tool of the present disclosure may include a densitometer 2015 (e.g., a vibrating tube densitometer or any other suitable densitometer) to measure fluid density which may be used to calculate compressibility. The fluid compressibility, k, can be calculated by precisely measuring the fluid density while varying the pressure.

Figure 3B:
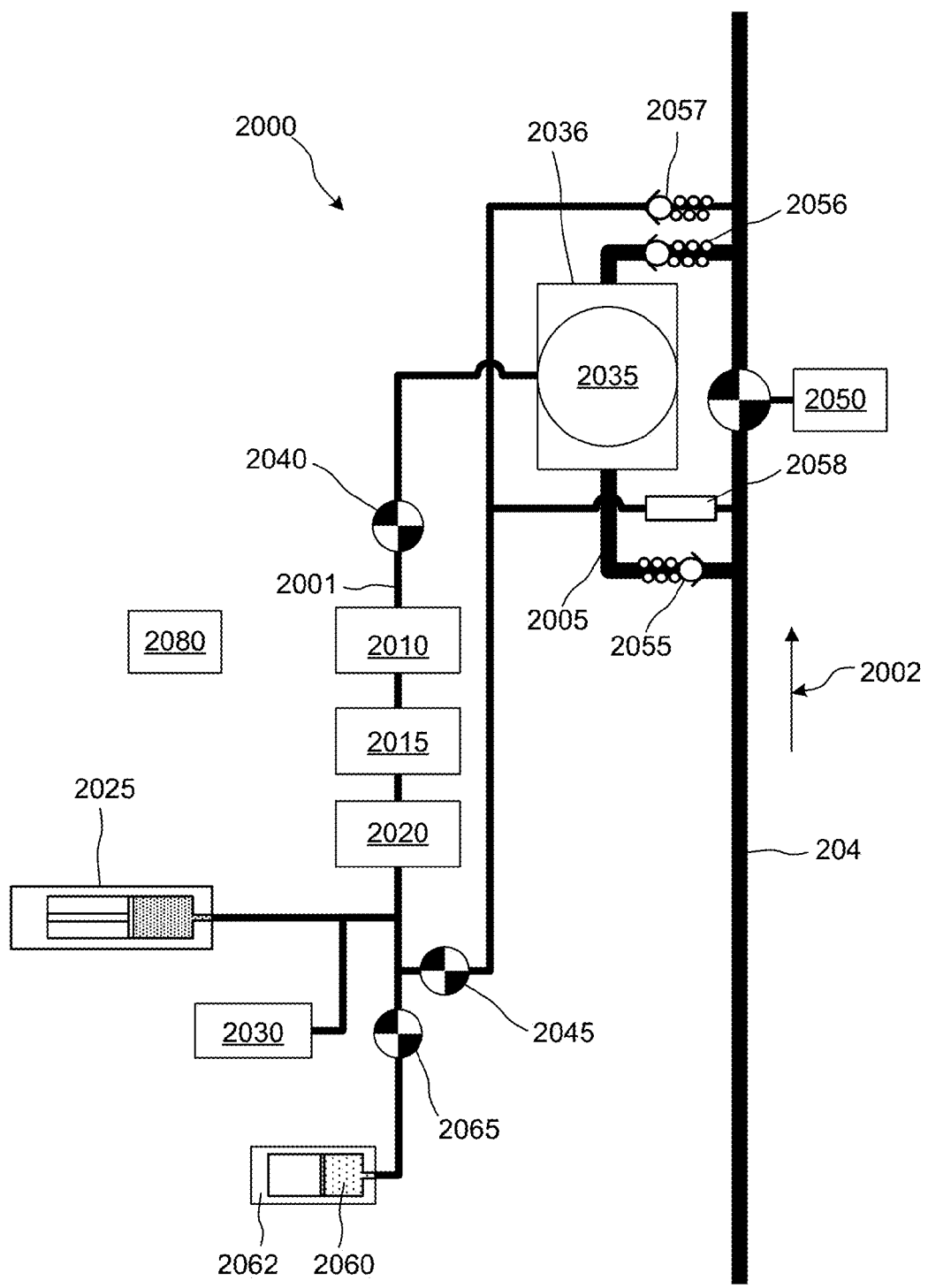
FIG. 3B is a schematic drawing of the fluid analysis system of FIG. 3A when reconfigured for reverse flow direction.
Figure 4:
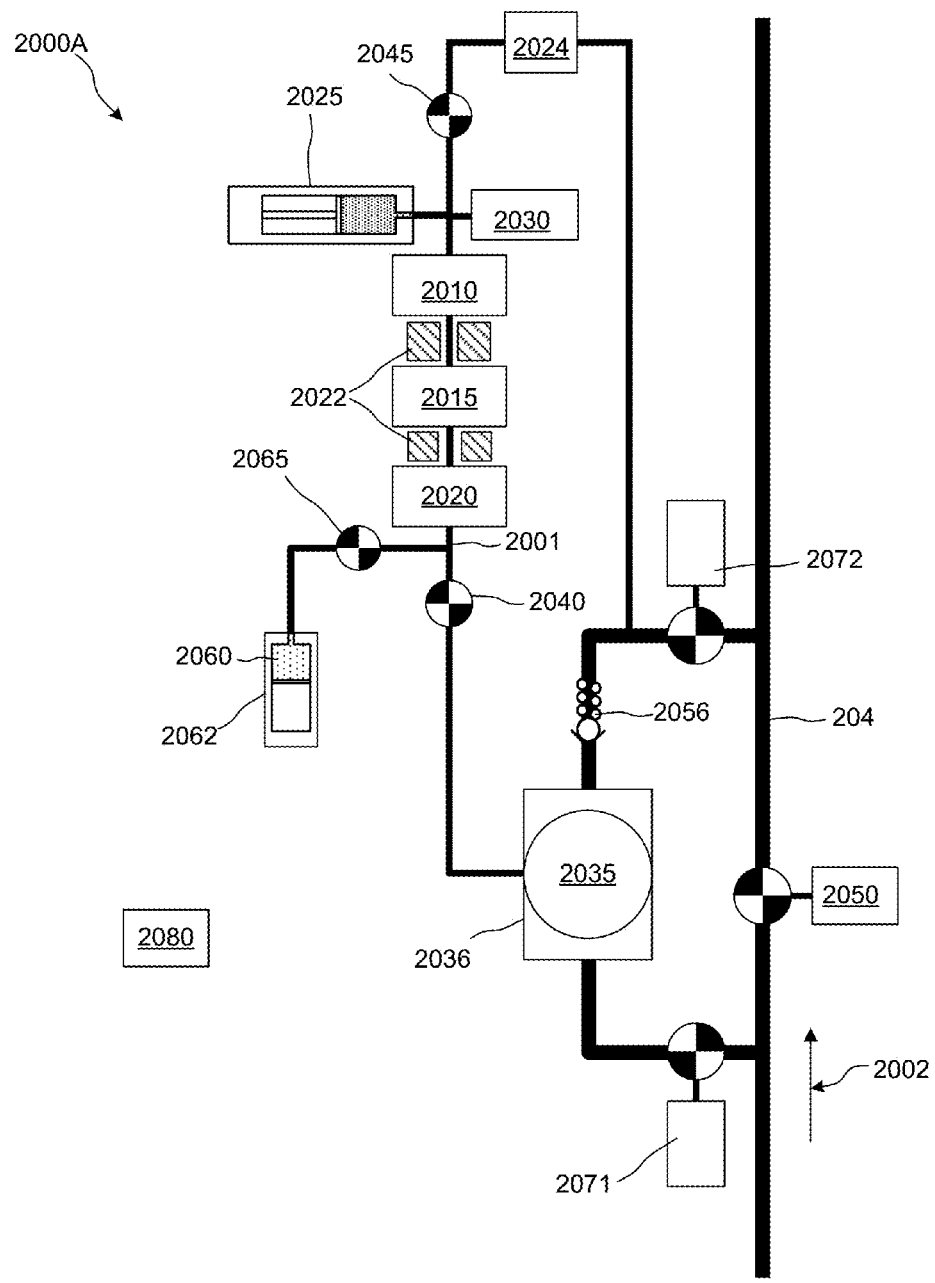
FIG. 4 is a schematic drawing of a fluid analysis system according to example embodiments.

FIGS. 3A, 3B, and 4 provide schematic views of examples of the phase transition cell 2010 in combination with other elements. The components may be configured to work together or individually to observe a fluid sample. The devices present in the figures may be used in one system. They may be used individually in one system or a combination of some of them may be used. Each of the individual components may be in contact with the control system, which is shown schematically in FIGS. 3A, 3B, and 4 as element 2080. The control system is in contact with the components and with an operator who is using a computer at the surface of the formation or other location. The control system is electronic and may control the mechanics of the components. Throughout the elements, several temperature sensors may be embedded in devices or tubing connections to observe the temperature of the fluid.

As indicated above, in some examples, the fluid is collected through a membrane 2035. The membrane 2035 is housed in a frame 2036 configured for supporting the membrane 2035 even during exposure to harsh environments and for cleaning activities, which may include, for example, backflushing to remove particulate buildup from the membrane 2035. In some examples, the membrane 2035 prevents particles with a dimension of 10 micron or greater to flow through the membrane. In some examples, the membrane 2035 is hydrophobic. As illustrated, the fluid is flowed through the membrane 2035 in a cross-flow configuration. In some embodiments, fluid is flowed across the membrane 2035 in a dead-end filtration configuration.

It is noted that the orientation of the flow direction 2002 is reversed (upward, or pumping up) in the examples of FIGS. 3B and 4 with respect to the examples of FIG. 3A (downward). In this regard, it should be appreciated that any suitable direction of flow with respect to the formation may be provided.

In order to divert fluid from the flow line 204, a flow line valve 2050, e.g., a motor valve or any other suitable valve, is partially or fully closed to at least partially restrict flow of the fluid up the flow line in the direction indicated by arrow 2002. This creates an increase in the pressure of the fluid in the flow line 204 upstream (in this example, above) the flow line valve 2050 (relative to the pressure above the valve 2050), which causes the fluid to flow through a check valve 2056 into bypass flowline 2005 and across the membrane 2035. Due to the selective permeability of the membrane 2035 (e.g., hydrophobicity to prevent water from passing through the membrane 2035), portions of the fluid that are allowed to pass through the membrane 2035 are directed to an entry valve 2040, while portions that are not allowed to pass through the membrane 2035 are directed back to the flow line 204 downstream (in this example, below) the line valve 2050 through another check valve 2056.

After the fluid passes through the membrane 2035, it flows through tubing to the entry valve 2040. The entry valve 2040 may be a needle valve or ball valve or other valve that is selected for its volume and fluid flow properties. The entry valve 2040 features a small dead volume and precise open and close control. The entry valve 2040 is controlled to allow or prevent a specific fluid flow to the phase transition cell 2010 and/or to allow backflushing of the membrane 2035. The valve 2040 may be closed completely in some operations. In some examples, the valve 2040 is modular to facilitate repairs and interchangeability. In the illustrated example, the entry valve 2040 is at least partially opened to allow the fluid to flow to the various sensors of the fluid analysis system 2000.

In the illustrated configuration, the fluid first flows through the phase transition cell 2010 as described above. From the phase transition cell 2010, fluid flows through the densitometer 2015. In some examples, the small volume of the fluid flowing through the densitometer 2015 utilizes a carefully selected cross sectional area and fluid flow path. The risk of deposition and/or flocculation of asphaltenes and other highly viscous or readily precipitating material on the densitometer and other sensors is a consideration that is addressed below. One example of such a densitometer 2015 is described in U.S. Patent Application Publication No. 2010/0268469, which is incorporated herein by reference in its entirety. It should be understood, however, that any other suitable densitometer may be provided.

Next, the fluid flows through the viscometer 2020. As with the densitometer 2015, the viscometer 2020 contains a small volume of fluid and may utilize a carefully selected cross sectional area and fluid flow path. A similar risk of surface contamination exists and is further discussed below. One example of such a viscometer 2020 is described in U.S. Patent Application Publication No. 2013/0186185, which is incorporated herein by reference in its entirety.

The fluid may be driven across the sensor elements 2010, 2015, and 2020 via piston 2025 or any other suitable mechanism. For example, the entry valve 2040 would be opened, an exit valve 2045 would be closed, and the piston 2025 actuated to draw in fluid. This drawing in of fluid causes fluid, in this valve configuration to travel across the elements 2010, 2015, and 2020.

The fluid that enters the pressure control device 2025, such as, for example, a micro piston, exerts a pressure on the pressure gauge 2030. In some examples, the pressure gauge 2030 can measure small pressure changes with a precision better than 0.1 psi and an accuracy of 2 to 3 psig under downhole conditions. In some examples, the gauge 2030 has low volume for its external housing and also has low dead volume of about 0.5 mL or less. The pressure gauge 2030 may be used by the control system as, for example, feedback to control the pressure exerted by the pump 2025.

After the fluid has been analyzed at elements 2010, 2015, and 2020, it is directed back to the flow line 204 via exit valve 2045, which is opened to allow flow. Like the entry valve 2040, the exit valve 2045 may be a needle valve or other valve that may be selected for its volume and fluid flow properties. In some examples, the exit valve 2045 features a small dead volume and precise control. The exit valve 2045 is controlled to allow or prevent a specific fluid flow to a back pressure regulator, such as check valve 2057. In some examples, a back pressure regulator may be omitted. In some examples, the fluid is driven back to the flow line 204 through the exit valve 2045 by closing the entry valve 2040, opening the exit valve 2045, and pushing the fluid 2025 from the piston 2025.

The fluid line after the exit valve 2045 also includes a parallel branch that includes a plug 2058 and is in fluid communication with the flow line 204 upstream (in this example, above) the flow line valve 2050. In this arrangement, it is possible, with minor modification of the placement and/or orientation of the back pressure regulators (in this example, check valves 2055, 2056, and 2057) and plug 2058 to operate the PVT apparatus when the flow through the flow line 204 is in a direction that is opposite to the flow direction depicted by arrow 2002 in FIG. 3A (i.e. downward in the drawing of FIG. 3A). To do so in the illustrated configuration would only involve reversing the flow orientation, or swapping position, of each of the back pressure regulators/check valves 2055 and 2056, and swapping the position of back pressure regular/check valve 2057 and plug 2058. This configuration is illustrated in FIG. 3B, which also shows the corresponding downward flow direction 2002.

The exit valve 2045 may be closed completely or partially in some operations. As with other valves described herein, valve 2045 may be modular in some examples to allow for, e.g., ease of repairs and interchangeability.

In, for example, the system 2000 shown in FIG. 3A, the fluid flows downwardly through the main flow line 204. The fluid may be driven through bypass flow line 2005, across the membrane 2035, through the microfluidic line 2001, and back into the main flow line 204 by a pressure-driven process in some examples. In this regard, the illustrated configuration provides a fluid pressure in flow line 204 above the flow line valve 2050 that is greater than the flow line 204 pressure below the valve 2050, due to at least partially closing valve 2050. Since the inlet to the system 2000 (i.e., the leg of the bypass line 2005 that flows across check valve 2056 and into membrane 2035) is connected to the higher pressure region of flow line 204 above valve 2050, and the outlet of system 2000 (i.e., the leg of the line flowing across valve 2057) is connected to the lower-pressure region of flow line 204 below valve 2050, a pressure gradient is provided and drives the fluid through the membrane 2035 and analysis modules 2010, 2015, and 2020 without any active pumping, resulting in a pressure-driven flow.

Likewise, pressure-driven flow may be utilized in the configuration of FIG. 3B, where the fluid is being pumped upwardly. In this arrangement, the higher pressure side of flow line 204 is below valve 2050 and the lower pressure side of flow line 204 is above valve 2050, with the system inlet and outlet locations being reversed with respect to what is shown in FIG. 3A. That is, the inlet (across check valve 2055) is in the high pressure region below valve 2050, and the outlet (across check valve 2057) is in the lower pressure region above valve 2050.

In other processes, the system 2000 (for example) utilizes a volumetric flow via opening and closing various valves together with actuation of the piston 2025 to pull or push fluid through the components of the system. Generally, the valve configuration for pumping fluid into the fluid analysis system 2000 is the entry valve 2040 opened and exit valve 2045 closed, and the configuration for pumping out of the system (e.g., discharging used fluid) is the entry valve 2040 closed and the exit valve 2045 opened. Such processes are described in further detail in other portions of this description.

Regardless of whether pressure-driven or piston-driven, the flow rates across the analysis modules 2010, 2015, and 2020 in some examples is 10 microliters per second. In some examples, the flow rate is between 5 and 10 microliters per second. It should be understood, however, that other flow rates may be utilized. In some examples, the piston 2025 has a precision actuation mechanism (e.g., a lead screw or ball screw) that allows for precise control of volumetric flow during piston-driven flow processes.

As mentioned above, components of the fluid analysis system 2000 are subject to contamination due to deposition and/or flocculation of asphaltenes and other highly viscous or readily precipitating material. Such components include, for example, the phase transition cell 2010, the densitometer 2015, and the viscometer 2020. In addition to negatively impacting the operation of such elements, this contamination can also contaminate later-introduced fluid samples, thereby causing measurements to potentially not accurately reflect the properties of the virgin reservoir fluid that is the subject of analysis.

Example embodiments provide for cleaning and/or flushing of the micro-flow lines 2001 and devices in the fluid analysis system 2000 using the following methods alone or in combination: applying pulsed electric or magnetic fields to the micro-flow lines and devices; application of chemical solutions to the micro-flow lines and devices; and microwave/ultrasonic heating of the micro-flow lines and devices.

The current dominating methods to reduce viscosity of crude oil for transportation and processing are heating and dilution with gasoline and diesel. The heating method is slow and energy intensive. For off-shore transportation, operators may use a drag-reducing agent but such agents are expensive and may raise concerns at a refinery. For downhole application, thermal methods such as steam flooding, aquathermolysis, in-situ combustion, and steam-assisted gravity drainage have been successful but also nonthermal methods such as microbial enhanced oil recovery, polymer flooding, and solvents processes. However, microbial "sludge" can plug the formation and have temperature limitations. Ionic liquids can reduce the viscosity of crude oil and extend this temperature limitation. They can have a catalytic effect on cracking and conversion of heavy hydrocarbons to light hydrocarbons (viscosity reduction of 34% with 1-butyl-3-methylimidazolium perchlorate).

For the fluid analysis system 2000, cleaning the micro-flow line one station after another allows for proper measurement quality. Flushing may become an issue with viscous reservoir fluids so reduction of the viscosity after measuring the crude oil physical properties can ensure proper flushing sampling one station after another. For this application, the volume required to flush/clean the micro-flow line sampling one station after another is small, which is cost-beneficial. A description of different cleaning methods are described below.

One cleaning mechanism is application of a pulsed electric or magnetic field. The pulsed field aggregates for a few hours paraffin or alphaltene particles into large aggregations of particles, thereby changing the rheological properties of the crude oil. The electric field is typically more successful for asphalt-base crude oil and mixed crude oil, while the magnetic field effectively reduces the viscosity of paraffin-base crude oil. If the paraffin has a ring structure, it is then diamagnetic and sensitive to a magnetic field. If the paraffin does not contain ring structure, the pulsed magnetic field will not reduce the crude oil viscosity and a pulsed electric field should be applied in this case.

The electric or magnetic field should be strong enough for the molecules to overcome the thermal Brownian motion. However, the field should also be applied in such a short pulse that the interaction does not have enough time to affect particles separated by macroscopic distances, but has enough time to assemble nearby particles together. During the application of the field, the viscosity changes rapidly. However, after the magnetic field is turned off, the suspension has a reduced viscosity, the dipolar interaction disappears, and the aggregated particles gradually disassemble under the Brownian motion. Therefore, the viscosity is expected to increase gradually and will return to the original value after all aggregated particles disintegrate.

The viscosity can be further reduced if the flow and the field direction are parallel.

For instance, the electric field applied for asphalt-base crude oil should be at least 0.9 kV/mm and the duration around 2 seconds, although applications of other fields may be provided in some examples. The field parameters may be optimized depending upon the targeted crude oil viscosity and flow line geometry. The electric field can be extremely efficient and can decrease the viscosity of crude oil so that, in some examples, the flow rate is doubled only two seconds after applying the electric field.

In some examples, the electric or magnetic field is generated just after the phase transition cell 2010 in the micro-flow line and the micro-piston 2025 would mix the fluid inside the micro-flow line by moving the fluid back and forth in the line, but there is no reason to preclude this system to be placed somewhere else inside the micro-flow line.

Another cleaning mechanism involves applying chemical solutions to clean/flush the microfluidic flow line. Some non-limiting examples of such solutions are solvents, polymers, surfactants, and catalysts.

Crude oil viscosity can be reduced significantly by dissolving in a solvent. Propane and butane have been used to reduce heavy oil viscosity. $CO_2$ cyclic injection has been used to increase oil production. Other solvents to reduce crude oil viscosity include toluene, pentane, methane/propane mixes, diesel, and kerosene. The effect of solvent viscous fingering, if an issue with particular solvents, can be addressed in the fluid analysis system 2000 micro-flow line by moving the piston 2025 back and forth and inducing mixing.

Polymers such as the poly(divinyl benzene-methyl octadecyl acrylate) nanoviscosity reducer have decreased crude oil viscosity up to 80%. Highly viscous polymers such as polyacrylamide capable of withstanding up to 200° C. should be able to displace heavy oil in the micro-flow line of the fluid analysis system 2000. They can then be broken using polymer breakers or oxidizer (bromate for the polyacrylamide, for example). Viscosity reduction can be achieved through emulsification: visco-elastic surfactant, or VES, can produce a highly viscous polymer with a low interfacial tension capable of displacing heavy oil inside the micro-flow line 2001 including the micro sensors. Its relatively low thermal stability (below 160° C.) could be used to break the gel using the Pt—Ir wire as heating source inside the phase transition cell 2010 of the flow line.

Catalysis is another mechanism for cleaning the flow line 2001 and micro sensors.

In heterogeneous catalysis, a solid catalyst can be placed after a valve after the last sensing element (e.g., the viscometer 2020 in the illustrated example 2000) so that its exposure to the fluid is effective only after the measurements were performed and mixing of fluid achieved as a result of to the micro-piston moving back and forth. A high level of crude oil viscosity reduction ratio may be attained by using carbon nanocatalysts at, for example, 150° C. Viscosity reduction can also be achieved with metal or metal oxides. Moreover, in some examples, there is a synergistic effect on the viscosity reduction between carbon nanocatalysts and microwave radiations.

Hydrogenation and catalytic cracking can be used to decrease the crude oil viscosity and therefore cleaning the micro-flow line 2001 and micro sensors 2010, 2015, and 2020. For that, transition metal catalyst such as, for example, nickel molybdenium or cobalt can be used as catalyst to speed up the reaction at temperatures downhole. Retro-Claisen reaction can also be used to achieve viscosity reduction (transition metal catalyst may be, for example, $FeCl_3$ or Fe derivatives, or Cobalt, etc. or the base may be $NaHCO_3$, AcONa, AcOK, BzOK, $Et_2NH$, NaOEt, etc.).

Homogeneous catalysis may also be provided as a cleaning mechanism. For example, Ionic liquid base nickel (e.g., 500 ppm) has been shown to decrease heavy oil viscosity significantly.

Microbial processes provide a further cleaning mechanism for the micro flow lines and sensors. In some examples, microorganisms are used to clean the micro flow line and sensors to break the heavy oil.

Moreover, the injection of a fluid (solvent, polymer, etc.) into the micro flow line 2001 with a measurable viscosity, density, and/or optical signature different from the formation fluid in the micro flow line 2001 allows analysis of the flow of the injected fluid as a "tracer" in accordance with some examples. This allows verification of flow through the membrane 2035 and into the micro flow line 2001. In accordance with some examples, a measurement is taken of the time it takes for the injected fluid to progress from sensor to sensor along the known volume of the micro flow line 2001 and the flow rate is estimated based on this measurement.

The same "cleaning solution" (chemical—solvent, polymer, etc) can be used to flush the micro line and components as well as the membrane 2035 by being forced backwards through the membrane 2035 to clean the membrane 2035.

In some examples, the system 2000 is provided with a reservoir 2060 configured to hold a solvent or other cleaning substance described above (e.g., polymer, surfactant, catalyst, etc.). Although the reservoir may be referred to herein as a "solvent reservoir" it should be understood that in some examples, the reservoir may be filled with the other cleaning fluids in addition to or as an alternative to solvents. In the illustrated example, the solvent reservoir 2060 is configured as the internal volume of a piston housing 2062, although other configurations may be provided.

Figure 3C:
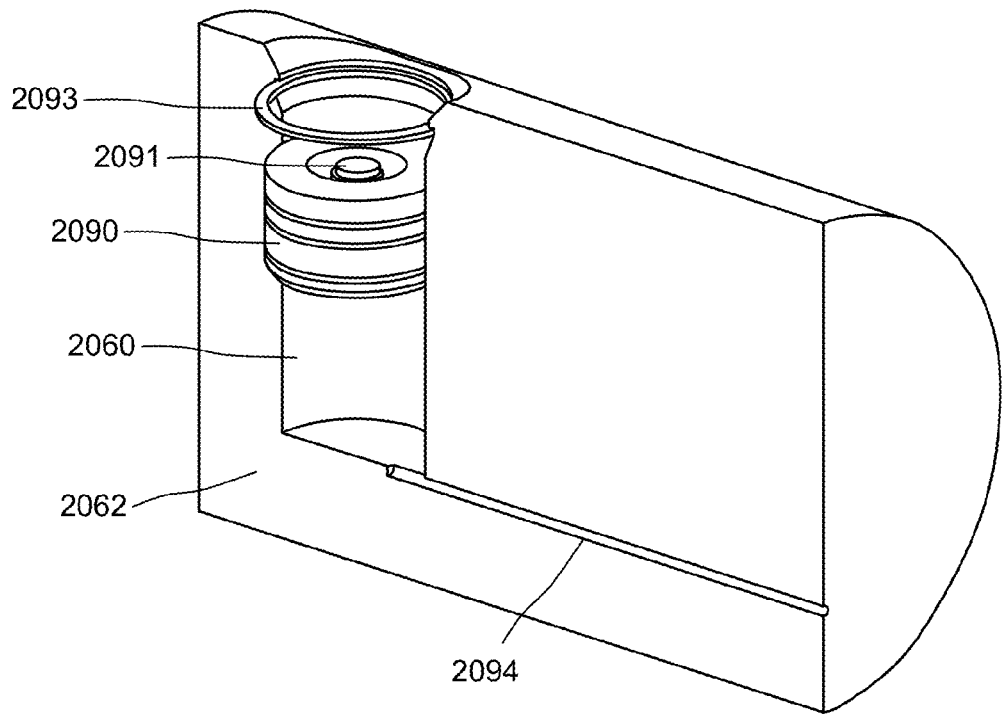
FIG. 3C shows a solvent reservoir of the fluid analysis system of FIG. 3A.

The fluid reservoir 2060 is shown in further detail in FIG. 3C. In this illustrated example, a compensation piston 2090 of fluid reservoir 2060 is in pressure communication with an external fluid, e.g., drilling mud, which occupies space that is created behind the piston as the solvent is extracted from the reservoir 2060. In some examples, the external fluid corresponds to a borehole fluid and/or the ambient pressure in the borehole. It should be understood, however, that other suitable configurations may be provided. Although the fluid reservoir 2060 is provided in connection with a piston 2090 in the illustrated example, other non-limiting examples provide collapsible non-rigid bladders or canisters to contain the solvent or other cleaning fluid.

Compensation piston 2090 compensates for volume change of the solvent (and/or any other suitable flushing fluid) due to, for example, pressure change or temperature change, thereby balancing pressure to the borehole. This is because, as indicated above, the side of the compensation piston 2090 opposite the solvent/fluid is in some examples in pressure communication with a borehole fluid corresponding to the pressure in the borehole. A relief valve 2091 of the compensation piston 2090 operates to relieve excess volume of solvent when, for example, there is a temperature increase without a corresponding pressure increase, which would expand the volume of the solvent/flushing fluid. This simple mechanism maintains solvent/flushing fluid pressure equal to borehole pressure passively without any active controller. It should be understood, however, that other examples may implement an active controller and/or any other suitable mechanism for balancing pressure.

In the example of FIG. 3C, the piston housing 2062, which is shown in cross-section, constitutes part of a tool body that is disposed in a borehole environment. The housing 2062 also includes a solvent/flushing fluid line 2094 that leads the fluid in the fluid reservoir 2060 to the microfluidic line 2001.

The compensation piston 2090 is retained in the piston housing 2062 by a retaining ring or stopper ring 2093.

The solvent is introduced to the various sensors via a valve 2065, which is opened to allow flow. In some examples, after the micro piston 2025 expels the used fluid, the exit valve 2045 is closed and valve 2065 is opened, with entry valve 2040 remaining closed. The micro piston 2025 then retracts to draw the solvent across the valve 2065 and into the chamber of the piston 2025.

After the solvent is drawn into the piston 2025, the entry valve 2040 is opened and valve 2065 is closed, with exit valve 2045 remaining closed. The piston 2025 is then actuated to expel the solvent across the phase transition cell 2010, the densitometer 2015, the viscometer 2020, and the entry valve 2040. In the illustrated configuration, the solvent then travels across the membrane 2035 and into the flow line 204. Because of the orientation of the check valves 2055 and 2056, the solvent flows into the flow line 204 at a position above the motor valve 2050. It should be understood that some examples may be configured to re-use solvent at least once. Such arrangements may include a secondary solvent reservoir where the used solvent may be directed instead of being directed back into the flow line 204.

Moreover, it should be appreciated that in some examples, the solvent reservoir may be actuated to drive the solvent across the sensor devices 2010, 2015, and 2020 independently of piston 2025. In such arrangements, the solvent reservoir may be a micropiston with features analogous to piston 2025.

After the sensor devices 2010, 2015, and 2020 have been flushed with the solvent, the fluid analysis system 2000 may proceed with drawing in and sampling the next fluid sample from the flow line 204 in the manner described above.

Figure 6A:
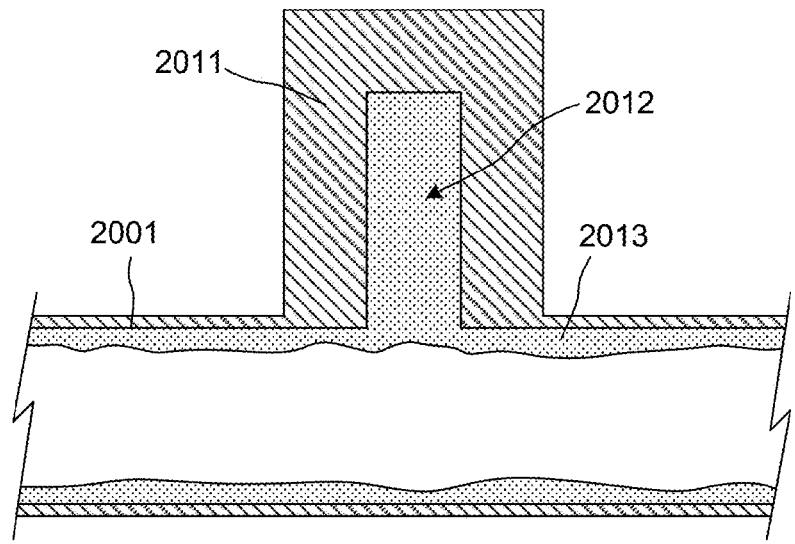
FIG. 6A is a schematic drawing of a sensor and a portion of a microfluidic flow line.

Referring to FIG. 6A, in some examples, one or more of the sensor devices 2010, 2015, and 2020 (one of which is schematically illustrated as sensor device 2011) includes a dead volume 2012 that is not directly within the flow path of the microfluidic line 2001. As shown in FIG. 6A, the inner surface of the microfluidic line 2001 and the dead volume 2012 are coated or filled with contamination 2013.

Figure 6B:
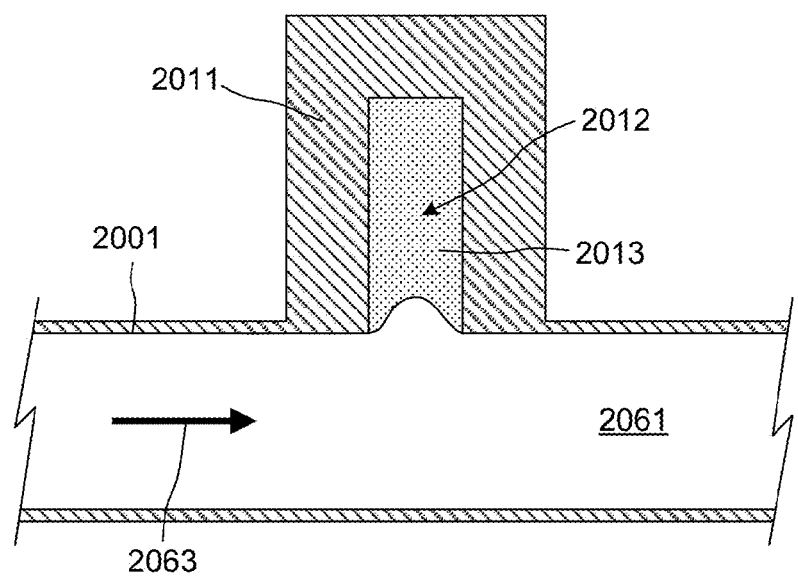
FIG. 6B shows the sensor and flowline of FIG. 6A after flowing a solvent through the flow line.

FIG. 6B shows the arrangement of FIG. 6A after a flushing fluid, in this example solvent 2061, been flushed through the microfluidic line 2001 in a left-to-right direction as illustrated by arrow 2063. The flushing of the solvent through the line 2001 has removed the contamination 2013 from the inner surface of the line 2001, but has removed only a small portion of the contamination 2013 in the dead volume 2012. This is due to the fact that the dead volume 2012 is outside of the flow path of the solvent 2061, especially where the flow of solvent 2061 is laminar.

In some examples, the contamination 2013 in the dead volume 2012 of sensor 2011 (and/or any other dead volume along the flow line 2001) may be removed by a pressure variation cycle. In order to do so, the flow line 2001 is isolated such that the operation of the piston 2025 can selectively raise and lower the pressure. For example, in the system of FIG. 3A, the entry and exit valves 2040 and 2045 and the solvent valve 2065 are closed, either completely or at least substantially enough to allow the actuation of the piston 2025 to raise and lower the pressure in the line 2001 to sufficiently high and low levels needed for the pressure variation cycle.

Figure 6C:
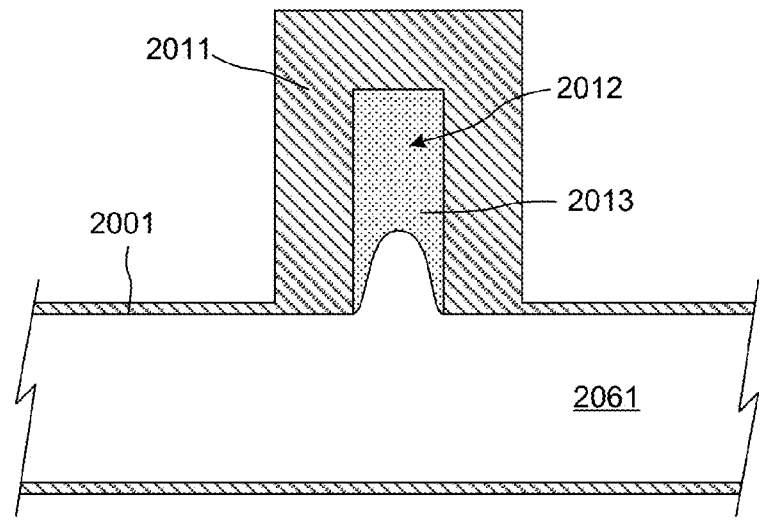
FIG. 6C shows the sensor and flow line of FIG. 6B during a pressurization of the flow line.

Referring to FIG. 6C, the appropriate valves have been closed and the piston 2025 actuated to increase the pressure in the line 2001. This increased pressure causes compression of the contamination 2013, which is schematically illustrated by the reduced volume of contamination 2013 shown in FIG. 6C as compared to that shown in FIG. 6B. After this compression, the pressure in the microfluidic line is reduced, for example, by actuation of the piston 2025. This reduction in pressure causes the contamination 2013 in the dead volume 2012 to expand from its compressed state. This expansion results in loosening and/or breaking apart of the contamination. This compression/expansion (or pressurization/depressurization) cycle may be repeated multiple times, although in some examples it is performed only a single time.

Figure 6D:
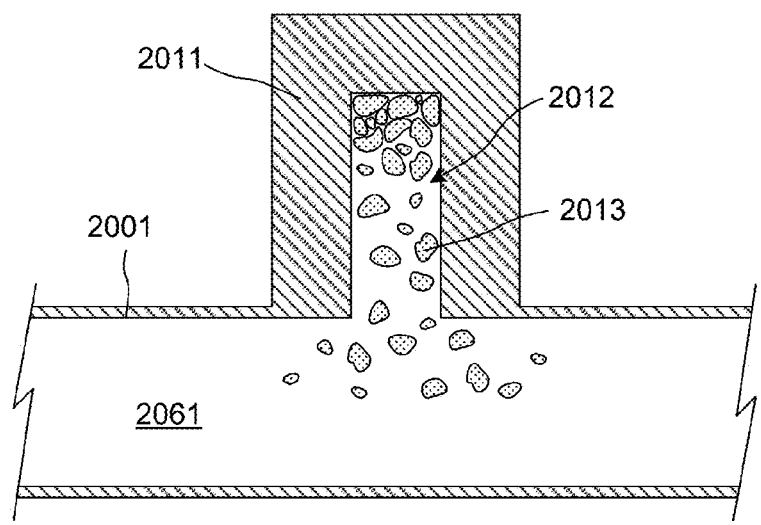
FIG. 6D shows the sensor and flow line of FIG. 6C after one or more pressurization/depressurization cycles.
Figure 6E:
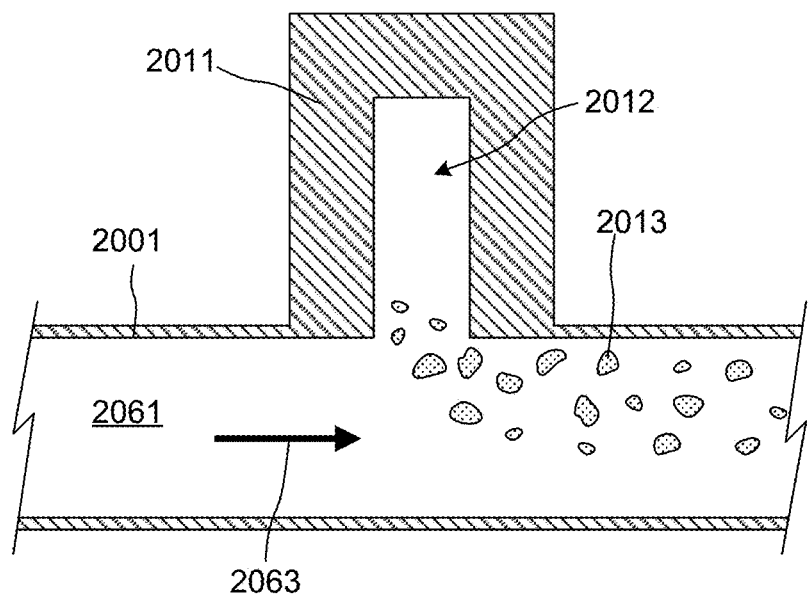
FIG. 6E shows the sensor and flow line of FIG. 6D after flowing a solvent through the flow line.

FIG. 6D shows the contamination 2013 after having been loosened/fragmented by the one or more compression/expansion cycles. As illustrated, the contamination 2013 is now floating into the flow stream of the microfluidic line 2001. Referring to 6E, the solvent 2061 is flowed in the direction of arrow 2063 to flush out the remaining contamination 2013 from the dead volume 2012. In the example of FIG. 3A, this is achieved by opening entry valve 2040 and pushing the solvent 2061 through the line 2001 by actuating piston 2025.

Although the example of FIGS. 6A to 6E apply the compression/expansion cycle(s) after the solvent has flowed through sufficiently to clean the interior of the flow line 2001, it should be understood that in some examples, the one or more compression/expansion cycles may be performed prior to completely flushing the contamination from the wall of the flow line 2001.

In some examples, pressure cycles having rapid depressurization are utilized to assist with dislodging and flushing contamination 2013 in the flow line 2001, dead volumes 2012, and/or the membrane 2035. For example, the flow line 2001 between entry and exit valves 2040 and 2045 may be isolated by closing the valves 2040 and 2045. In some examples the piston is actuated to maximize or substantially increase the pressure in the flow line 2001 between valves 2040 and 2045. After this pressurization, one or more of the valves, e.g., valve 2040 and/or valve 2045, is rapidly opened to cause a rapid depressurization to assist with releasing and expelling contamination 2013. This depressurization may be considered analogous to a sneeze, or sturnutation. In some examples, the entry valve 2040 is rapidly opened in order to cause the depressurization. In some examples, this release of pressure causes a rapid increase in pressure between the entry valve 2040 and the membrane 2035, which may be utilized to dislodge and/or expel contamination 2013 from the membrane 2035 in addition to facilitating removal of contamination from the line 2001 between valves 2040 and 2045.

In some examples, after closing of the entry and exit valves 2040 and 2045, the flow line 2001 between the valves 2040 and 2045 is maximally or substantially depressurized relative to the flow line external to the portion between valves 2040 and 2045. In some examples, this depressurization is attained by actuation of the piston 2025. While the line 2001 is in this depressurized state, one or more of the valves is rapidly opened in order to rapid drop the pressure in one or more portions of the line 2001 external to the portion between valves 2040 and 2045. For example, in systems 2000, 2000A, and 2000B, the entry valve 2040 may be rapidly opened in order to rapidly reduce the pressuring the line 2001 between the membrane 2035 and the entry valve 2040. This rapid pressure reduction may by utilized to clean and/or or disengage contamination 2013 from the membrane 2035. This may be achieved in some examples due to the resulting rapid decrease in pressure on one side of the membrane 2035 (the side in communication with microfluidic line 2001) relative to the opposite side of the membrane 2035 (the side in communication with the bypass line 2005). It is noted that this procedure may be performed with any suitable fluid in the flow line 2001, even the formation fluid that is being tested.

In some examples that utilize the aforementioned pressurization/depressurization, the pressure in the isolated portion of the flow line 2001 is greater or less than the pressure in one or more of the non-isolated adjacent portions of the flow line 2001 by 1000 psi or more. In some examples, the difference in pressure is 2000 psi or more. In some examples, the difference in pressure is 3000 psi or more. In some examples, the difference in pressure is 4000 psi or more. In some examples, the difference in pressure is 5000 psi or more.

The solvent reservoir 2060 may be dimensioned to hold a sufficient volume of solvent to allow for a desired number of samples to be tested. In some examples, the sensor devices 2010, 2015, and 2020 are cleaned between each fluid sample, where some examples are configured to flush the sensor devices 2010, 2015, and 2020 less frequently, e.g., between every other sample or based on some feedback from the system 2000 (e.g., signal quality from sensor devices 2010, 2015, and 2020).

FIG. 4 shows a fluid analysis system 2000A that shares features in common with the fluid analysis system 2000 of FIGS. 3A and 3B except to the extent indicated otherwise.

The fluid analysis system 2000A includes many of the same components as the fluid analysis system 2000, but differs in arrangement. One difference between these systems is that in system 2000A the sensor devices 2010, 2015, and 2020 are disposed between the micro piston 2025 and the solvent reservoir 2060. Thus, in the apparatus 2000A of FIG. 4, the solvent is pulled across the sensor devices 2010, 2015, and 2020 by retraction of the micro piston 2025, as opposed to being pushed or expelled from the micro piston 2025 as in the apparatus 2000 of FIGS. 3A and 3B.

Further, the apparatus 2000A includes two additional motor valves 2071 and 2072 on opposite sides of the membrane housing 2036. These valves 2071 and 2072 open and close access to the flow line 204 on respective sides of the flow line valve 2050.

The systems 2000 and 2000A have some differing characteristics. For example, in the apparatus 2000 of FIGS. 3A and 3B, the piston 2025 is able to drive the solvent in a single movement to flush the three sensor devices 2010, 2015, and 2020 and the membrane 2035. This configuration also allows the solvent to be back-flushed across the sensor devices 2010, 2015, and 2020 and the membrane 2035 by driving the solvent in a flow direction that is opposite that of the fluid sample as it travels from the membrane 2035 and through the sensors 2010, 2015, and 2020. Regarding the apparatus 2000A of FIG. 4, it is noted that the solvent reservoir 2060 is located at a position that in some examples allows the solvent to be driven back into the reservoir 2060 by expelling the solvent from the piston 2025 while entry and exit valves 2040 and 2045 are closed and solvent valve 2065 is opened.

In the examples of FIGS. 3A, 3B, and 4, the volume of liquid solvent is isolated from the microfluidic line 2001 by a valve 2065. Referring to the example of FIG. 4, to flush the microfluidic flow line 2001 with solvent, the valve 2065 would be opened and the micropiston 2025 would draw solvent into the microfluidic line 2001. The same micropiston 2025 would push the solvent out of the microline either back through the membrane 2035 (open the lower microline inlet valve 2040), back into the solvent reservoir to be used again, or out through the exit of the micro line into the bypass line 204 by opening the outlet valve 2045 on the microfluidic line 2001.

Referring to FIG. 4, the system 2000A further includes cleaning devices 2022. In some examples, cleaning devices 2022 are microwave sources configured to exert microwave or ultrasonic heating onto the microfluidic line 2001 in accordance with the microwave/ultrasonic cleaning processes described herein. In some examples, the cleaning devices 2022 are configured to exert pulsed electrical or magnetic fields onto the microfluidic line 2001 in accordance with the pulsed field cleaning processes described herein. Although two cleaning devices are shown, it should be understood that any number of cleaning devices 2022, including a single cleaning device 2022, may be provided and disposed at any suitable location(s) along the microfluidic line 2001.

The system 2000A further includes a catalyst 2024 disposed after the exit valve 2045 in accordance with the catalytic processes described herein.

Figure 5:
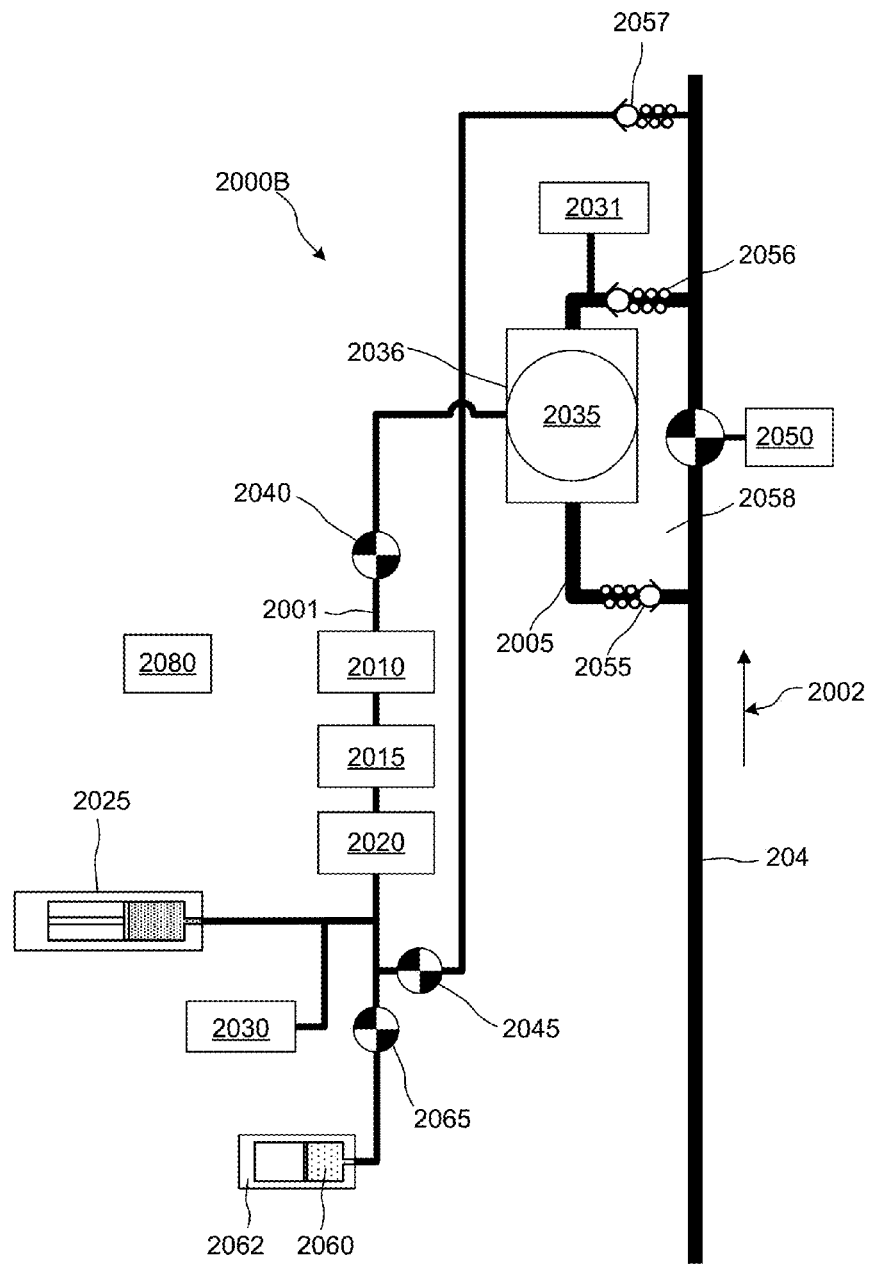
FIG. 5 is a schematic drawing of a PVT apparatus according to example embodiments.

FIG. 5 shows a fluid analysis system 2000B that shares features in common with the fluid analysis system 2000 of FIGS. 3A and 3B except to the extent indicated otherwise.

The system 2000B differs, for example, in that the flow line between exit valve 2045 and the main flow line 204 includes only a single leg, omitting the second leg and corresponding plug, instead having a single check valve 2057. This is a simpler layout for situations where this is not need to be able to adapt the system for opposite flow direction in the line 204.

The fluid analysis system 2000B differs from the system 2000 in that it includes a second pressure sensor 2031. The second pressure sensor 2031 is disposed on the bypass flow line 2005 at a location downstream from the membrane 2035. Accordingly, the pressure sensor 2031 is arranged and configured to monitor the pressure of fluid that is downstream of the membrane in the bypass line 2005.

As with the other example systems 2000 and 2000A, the reservoir 2060 includes a piston that is in communication with the borehole pressure on one side and the solvent (or other fluid) on the other side. Accordingly, the pressure of the fluid in the reservoir is pressure balance with the borehole pressure in these examples (although any suitable reservoir configuration may be provided in accordance with other examples).

As with example system 2000, the pressure unit 2025, e.g., a micro piston, is positioned close to exit valve 2045. The flushing operation of the system 2000B is generally the same as that described above with respect to system 2000. In this configuration, entry valve 2040 and exit valve 2045 are closed and valve 2065 is opened. At this stage, the piston 2025 is operated to draw clean solvent (or other fluid) into the piston 2025. After the solvent is drawn into the piston 2025, valve 2065 is closed and entry valve 2040 is opened. At this stage, the piston 2025 is actuated to expel the solvent through the microfluidic line 2001, across the sensors 2020, 2015, and 2010 and the membrane 2035. Because of the arrangement of check valves (or other suitable mechanisms in other examples), the solvent the flows, after passing across the membrane 2035 into the portion of the bypass line 2005 downstream of the membrane and toward or through the check valve 2056.

During the process of flushing the solvent across the sensors 2020, 2015, and 2010 and the membrane 2035, the pressure measured at pressure gauges 2030 and 2031 is monitored (e.g., by processing system 2080). If the pressure at gauge 2031 (i.e., on the downstream side of the membrane 2035 is higher than the pressure at gauge 2030 (i.e., the pressure in the microfluidic line 2010 at the outlet of the piston 2025, this may be interpreted as indicating the presence of clogging in the microfluidic line 2001 (including the sensors) and/or the membrane 2035. In some examples, the control system 2080 stops actuation of the piston 2025 when this clogging determination is made. This determination may be made by, for example, control system 2080 and may be made based on, for example, exceeding a threshold pressure difference between the gauges 2030 and 2031. In some examples, this threshold is set at a few hundred psi difference. In some examples, the threshold pressure difference is at least 100 psi. In some examples, the threshold pressure difference is at least 200 psi. In some examples, the threshold pressure difference is at least 300 psi.

The second pressure gauge 2031 also allows other monitoring functions regarding the condition and operation of the system 2000B. For example, when inlet valve 2040 is opened, if the pressure gauge 2031 measures a higher pressure than the pressure gauge 2030, this indicates the presence of conditions that would cause unintended reverse flow into the microfluidics line from the membrane side. In some examples, based on this detected condition, the control system 2080 may increase the pressure in the microfluidic line 2001 to prevent such reverse flow.

In some example systems 2000, 2000A, 2000B, the volume of the microfluidics line 2001, which is determined as the volume in the line 2001 disposed between the entry valve 2040 and the exit valve 2045, but not including the volume of the chamber of the piston system 2025, is less than 1 milliliter. In some examples, this volume is less than 500 microliters.

In some examples, the volume of the effective chamber of the piston 2025 (i.e., the maximum volume capacity of fluid that the piston is able to draw in or push out between extreme stroke positions) is at least twice the volume of the microfluidics line 2001.

In some examples, the volume of the solvent reservoir 2060 is more than 10 times the volume of the microfluidics line 2001. In some examples, the volume of the solvent reservoir 2060 is more than 20 times the volume of the microfluidics line 2001. In some examples, the volume of the solvent reservoir 2060 is more than 30 times the volume of the microfluidics line 2001. In some examples, the volume of the solvent reservoir 2060 is more than 100 times the volume of the microfluidics line 2001. In some examples, the volume of the solvent reservoir 2060 is more than 200 times the volume of the microfluidics line 2001.

By sizing the reservoir 2060 to have such a substantially larger volume than the microfluidics line 2001, the flushing system is able to perform the sensor/membrane flushing more than once at each fluid measurement point in downhole analysis.

Furthermore, the relatively large-volume reservoir 2060 in comparison to the microfluidic line 2001 facilitates use of the system 2000, 2000A, 2000B to provide a calibration function. In some examples, the reservoir is filled with a fluid (e.g., a solvent or any other suitable fluid) that has known properties corresponding to the properties measured by the sensors 2010, 2015, and/or 2020. As such, the sensors 2010, 2015, and/or 2020 may be calibrated by flushing the fluid as described above and taking measurements of the fluid using the sensors 2010, 2015, and/or 2020. Since the fluid properties are known, this allows the sensors 2010, 2015, and/or 2020 to be calibrated before or between measurements of reservoir fluids. By providing this localized calibration, the system 2000, 2000A, 2000B avoids having to run much larger volumes of calibration fluid through the main flow line 204. Moreover, because the large volume of calibration fluid in the reservoir 2060, a large number of such calibrations may be performed during operation of the tool between reservoir fluid analyses.

The calibration may occur, for example, after the sensors are cleaned with an initial flushing with the same fluid as used in the calibration. In some examples, the calibration fluid is provided separately from the cleaning/flushing fluid.

In some examples, an inline filter is disposed between the solvent reservoir 2060 and the valve 2065 to prevent any solids from transferring into the microfluidic line 2001 through the valve 2065.

In some examples, the flow line from the solvent reservoir 2060 includes a check valve to prevent reverse flow into the reservoir 2060 from the microfluidic line 2001. In some examples, the check valve can save operation time of valve 2065 during sensor cleaning operations.

In some examples, the solvent reservoir 2060 includes a pressure relief valve to prevent unexpected pressure charge in the reservoir 2060 due to, for example, temperature increase.

In some examples, when the solvent in the reservoir runs out and piston 2025 attempts to draw in additional solvent, the pressure gauge 2030 will read a drawdown pressure. The control system 2080 may recognize this condition and terminate or reverse the piston stroke. Such examples provide a safety mechanism to prevent borehole fluid from accidentally being drawn into microfluidics line 2001 via solvent chamber 2060.

Although many of the described examples herein describe the various systems 2000, 2000A, and 2000B utilizing a solvent as the fluid disposed in the reservoir 2060 for performing the various described processes, it should be readily apparent that the fluid used in these examples may be any suitable fluid as described herein. For example, the fluid may be the catalysts, polymers/surfactants, or microorganism solutions such as those discussed above.

Although the sensors 2010, 2015, and 2020 of FIGS. 3A, 3B, and 4 are arranged in a particular order, it should be appreciated that this ordering is one of multiple layouts of the sensors 2010, 2015, and 2020.

The solvent reservoir 2060 also allows for compensation of the micro flow line 2001 during tripping in and out of the borehole. In some examples, the micro flow line 2001 and sensors are pre-charged with the same solvent as in the solvent chamber 2060, the valves 2040 and are closed and the solvent chamber valve 2065 is left open. This traps the solvent in the micro flow line 2001 and solvent chamber 2060. As indicated above, the solvent chamber piston is compensated on the back side to borehole pressure (either by directly connecting it to the annular mud pressure or by connecting the back of the piston to compensated oil). Accordingly, as the tool is run in hole, the micro flow line is isolated from the membrane 2035 and main flow line which reduces the risk for contamination (solids) getting into the micro flow line 2001, protects the membrane 2035 by minimizing the volume of fluid that enters the micro flow line 2001 through the membrane 2035 as a result of running in hole. The pressure in the micro flow line 2001 is maintained at borehole pressure by the solvent chamber.

In some examples, the operation of a fluid analysis system, for example, a mini PVT apparatus 2000, 2000A as shown in FIGS. 3A, 3B, and 4 may occur with a total internal volume of 500 microliters or less. Some embodiments may have an internal volume in microfluidic line 2001 of 300 microliters or less, 100 microliters or less, 50 microliters or less, 30 microliters or less or 10 microliters or less. This apparatus is able to operate at pressure and temperatures consistent with downhole requirements and exploits novel sensors such as a microfluidic densitometer, a microfluidic viscometer, and a phase transition cell that uses thermal nucleation. The compatibility with true oilfield crude oils and measured a phase diagram that is consistent with that measured with a conventional view cell that use a comparatively large volume of fluid.

Further details of using the PVT apparatus in conjunction with a wellbore tool and methods for implementing the PVT apparatus are described in U.S. Patent Application Publication No. 2014/0260586 and PCT International Publication No. WO 2014/158376, each of which is incorporated herein by reference in its entirety.

The processes described herein, such as, for example, operation of valves and pistons and the performance of the various fluid analyses described herein, can be performed and implemented at least in part by a computer system.

The methods and processes described above such as, for example, operation of valves and pistons and the performance of the various described fluid analyses, may be performed by a processing system. The processing system may correspond at least in part to element 2080 described above. The processing system may include a single processor, multiple processors, or a computer system. Where the processing system includes multiple processors, the multiple processors may be disposed on a single device or on different devices at the same or remote locations relative to each other. The processor or processors may include one or more computer processors (e.g., a microprocessor, microcontroller, digital signal processor, or general purpose computer) for executing any of the methods and processes described above. The computer system may further include a memory such as a semiconductor memory device (e.g., a RAM, ROM, PROM, EEPROM, or Flash-Programmable RAM), a magnetic memory device (e.g., a diskette or fixed disk), an optical memory device (e.g., a CD-ROM), a PC card (e.g., PCMCIA card), or other memory device.

The methods and processes described above may be implemented as computer program logic for use with the computer processor. The computer processor may be for example, part of a system such as system 200 described above. The computer program logic may be embodied in various forms, including a source code form or a computer executable form. Source code may include a series of computer program instructions in a variety of programming languages (e.g., an object code, an assembly language, or a high-level language such as C, C++, Matlab, JAVA or other language or environment). Such computer instructions can be stored in a non-transitory computer readable medium (e.g., memory) and executed by the computer processor. The computer instructions may be distributed in any form as a removable storage medium with accompanying printed or electronic documentation (e.g., shrink wrapped software), preloaded with a computer system (e.g., on system ROM or fixed disk), or distributed from a server or electronic bulletin board over a communication system (e.g., the Internet or World Wide Web).

Alternatively or additionally, the processing system may include discrete electronic components coupled to a printed circuit board, integrated circuitry (e.g., Application Specific Integrated Circuits (ASIC)), and/or programmable logic devices (e.g., a Field Programmable Gate Arrays (FPGA)). Any of the methods and processes described above can be implemented using such logic devices.

Any of the methods and processes described above can be implemented as computer program logic for use with the computer processor. The computer program logic may be embodied in various forms, including a source code form or a computer executable form. Source code may include a series of computer program instructions in a variety of programming languages (e.g., an object code, an assembly language or a high-level language such as C, C++ or JAVA). Such computer instructions can be stored in a non-transitory computer readable medium (e.g., memory) and executed by the computer processor. The computer instructions may be distributed in any form as a removable storage medium with accompanying printed or electronic documentation (e.g., shrink wrapped software), preloaded with a computer system (e.g., on system ROM or fixed disk), or distributed from a server or electronic bulletin board over a communication system (e.g., the Internet or World Wide Web).

To the extent used in this description and in the claims, a recitation in the general form of "at least one of [a] and [b]" should be construed as disjunctive. For example, a recitation of "at least one of [a], [b], and [c]" would include [a] alone, [b] alone, [c] alone, or any combination of [a], [b], and [c].

Although a few example embodiments have been described in detail above, those skilled in the art will readily appreciate that many modifications are possible in the example embodiments without materially departing from embodiments disclosed herein. Accordingly, all such modifications are intended to be included within the scope of this disclosure.

What is claimed is:

1. An apparatus for measuring a property of a fluid sample that flows through an inlet line, comprising:
   a microfluidic flow line having a first end opposite a second end;
   an inlet valve fluidly coupled between the inlet line and the first end of the microfluidic flow line:
   an outlet valve fluidly coupled to the second end of the microfluidic flow line;
   at least one microfluidic sensor being disposed along the microfluidic flow line between the first end and the second end; and
   a fluid reservoir configured to store cleaning fluid, wherein the fluid reservoir is fluidly coupled to the microfluidic flow line;
   wherein the microfluidic flow line has a first configuration where the inlet valve and the outlet valve are configured in open states that allow the fluid sample to flow through the inlet valve into the microfluidic flow line and through the microfluid flow line in a first direction toward the second end and out the second end through the outlet valve, and the at least one microfluidic sensor is configured to measure at least one property of the fluid sample flowing in the first direction through the microfluidic flow line; and
   wherein the microfluidic flow line has a second configuration where the inlet valve is configured in its open state that allows cleaning fluid to move from the fluid reservoir into the microfluidic flow line and through the microfluidic flow line in a second direction toward the first end and through the inlet valve in order to remove unwanted contamination from the at least one microfluidic sensor.

2. The apparatus of claim 1, wherein the fluid reservoir is fluidly coupled to the second end of the microfluid flow line.

3. The apparatus of claim 1, further comprising a cleaning valve fluidly coupled between the solvent reservoir and the microfluidic flow line, wherein the cleaning valve has an open state that allows the cleaning fluid to flow from the fluid reservoir into the microfluidic flow line.

4. The apparatus of claim 1, wherein the cleaning fluid comprises a solvent.

5. The apparatus of claim 1, wherein pressure of the sample fluid in the inlet line drives the flow of sample fluid in the first direction through the microfluidic flow line in the first configuration of the microfluidic flow line.

6. The apparatus of claim 1, wherein the fluid reservoir comprises a compensation piston configured to passively equalize pressure of the cleaning fluid in the fluid reservoir with pressure of a borehole fluid external to the fluid reservoir.

7. The apparatus of claim 6, wherein the compensation piston comprises a relief valve configured to release a volume of cleaning fluid from the fluid reservoir in response to an increase in volume of the cleaning fluid.

8. The apparatus of claim 1, further comprising a hydrophobic membrane fluidly coupled between the inlet line and the inlet valve, wherein in the first configuration of the microfluidic flow line the fluid sample flows through the hydrophobic membrane before traveling to microfluidic flow line and the at least one microfluidic sensor.

9. The apparatus of claim 8, wherein in the second configuration of the microfluidic flow line cleaning fluid moves through the membrane to backflush the membrane.

10. The apparatus of claim 9, further comprising a piston fluidly coupled to the microfluidic flow line, wherein movement of the piston in the second configuration of the microfluidic flow line moves cleaning fluid through the microfluidic sensor and through the membrane in a single piston stroke.

11. The apparatus of claim 1, further comprising a piston fluidly coupled to the microfluidic flow line, wherein movement of the piston in the second configuration of the microfluidic flow line moves cleaning fluid from the fluid reservoir into the microfluidic flow line and through the microfluidic flow line sensor in the second direction toward the first end in order to remove unwanted contamination from the at least one microfluidic sensor.

12. The apparatus of claim 11, wherein the piston is further configured to control fluid pressure in the microfluidic flow line.

13. The apparatus of claim 11, wherein operation of the piston drives the flow of sample fluid in the first direction through the microfluidic flow line in the first configuration of the microfluidic flow line.

14. The apparatus of claim 11, further comprising:
a first pressure sensor configured to measure a first fluid pressure at an outlet of the piston in the second configuration of the microfluidic flow line; and
a second pressure sensor configured to measure a second fluid pressure of the cleaning fluid after it has been driven through the at least one microfluidic sensor in the second configuration of the microfluidic flow line;
a processing system configured to detect a clogged state of the at least one microfluidic sensor based on a comparison of the first and second fluid pressures.

15. The apparatus of claim 11, further comprising a control system configured to operate the inlet valve, the outlet valve, and the piston.

16. The apparatus of claim 15, wherein, for the second configuration of the microfluidic flow line, the control system is configured to sequentially (a) close the inlet valve and the outlet valve, (b) actuate the piston to draw the cleaning fluid from the fluid reservoir into the microfluid flow line and into the piston, (c) open the inlet valve and (d) actuate the piston to expel the solvent from the piston into the microfluidic flow line and across the at least one microfluidic sensor and through the inlet valve.

17. The apparatus of claim 16, further comprising a cleaning valve fluidly coupled between the fluid reservoir and the second end of the microfluid flow line, wherein the cleaning valve has an open state that allows the cleaning fluid to flow from the fluid reservoir into the microfluidic flow line, and wherein the control system configures the cleaning valve in its open state prior to actuating the piston to draw the solvent from the fluid reservoir into the microfluid flow line and into the piston.

18. The apparatus of claim 1, wherein the apparatus is part of a borehole tool and configured to operate in downhole conditions.

19. The apparatus of claim 18, wherein the at least one microfluidic sensor includes a plurality of sensors.

20. The apparatus of claim 19, wherein the plurality of sensors includes a phase transition cell.

21. The apparatus of claim 20, wherein the plurality of sensors further comprises a vibrating tube densitometer.

22. The apparatus of claim 21, wherein the plurality of sensors further comprises a vibrating wire viscometer.

23. A method comprising:
flowing a sample fluid through a microfluidic flow line in a first direction and into contact with a microfluidic sensor disposed along the microfluidic flow line;
measuring a property of the fluid sample using the microfluidic sensor; and
after measuring the property of the fluid sample, flushing the microfluidic sensor by flowing a cleaning fluid through the microfluidic flow line in a second direction that is opposite the first direction.

24. The method of claim 23, further comprising:
calibrating the microfluidic sensor using the cleaning fluid as a calibrant.

25. The method of claim 23, wherein the cleaning fluid comprises a solvent.

26. The method of claim 23, further comprising detecting a clogged state of the microfluidic sensor based on a detected pressure differential across the microfluidic sensor during the flushing.

27. The method of claim 26, further comprising, in response to the detected clogged state, stopping the flushing.

28. The method of claim 23, further comprising:
isolating a first portion of the microfluidic flow line;
pressurizing the isolated first portion of the microfluidic flow line relative to a second portion of the flow line outside the isolated portion; and
while the isolated first portion is pressurized, opening one or more valves separating the isolated first portion from the second portion to depressurize the isolated first portion.

29. The method of claim 28, wherein the pressurization of the isolated first portion results in a pressure differential having a magnitude of at least 3000 psi between the first and second portions.

30. The method of claim 28, wherein the pressurization of the isolated first portion results in a pressure differential having a magnitude of at least 5000 psi between the first and second portions.

31. The method of claim 23, further comprising:
isolating a first portion of the microfluidic flow line;

reducing pressure of the isolated first portion of the microfluidic flow line relative to a second portion of the flow line outside the isolated portion; and while the isolated first portion is at the reduced pressure, opening one or more valves separating the isolated first portion from the second portion to increase the pressure in the first portion while reducing the pressure in the second portion.

32. The method of claim 31, wherein the difference in pressurization of the isolated first portion results in a pressure differential having a magnitude of at least 5000 psi between the first and second portions.

33. The method of claim 31, wherein the reducing of pressure of the isolated first portion results in a pressure differential having a magnitude of at least 3000 psi between the first and second portions.

34. The method of claim 31, wherein the second portion of microfluidic flow line is in fluid and pressure communication with a selectively permeable membrane.

35. The method of claim 34, wherein the reducing the pressure in the second portion of the microfluidic flow line operates to remove contamination from the selectively permeable membrane.

36. The method of claim 23, wherein the flushing is performed by a piston.

37. The method of claim 36, further comprising, prior to flushing the microfluidic sensor, drawing the cleaning fluid into a chamber of the piston from a solvent reservoir.

38. The method of claim 37, wherein the cleaning fluid is drawn into the chamber of the piston while an inlet valve disposed at a first end of the microfluidic flow line is closed and an outlet valve disposed a second end of the microfluidic flow line opposite the first end is closed.

39. The method of claim 38, wherein a cleaning valve is in an open state when the cleaning fluid is drawn into the chamber of the piston and in a closed state when the cleaning fluid is expelled.

40. The method of claim 38, further comprising:
opening the inlet valve; and
expelling the cleaning fluid from the chamber of the piston and through the microfluidic flow line in order to perform the flushing of the microfluidic sensor, such that the cleaning fluid flows out of the opened inlet valve while the outlet valve remains closed.

41. The method of claim 40, wherein the expelling of the cleaning fluid from the chamber of the piston occurs in a single stroke of the piston and wherein during the single stroke of the piston, the cleaning fluid is further pushed through a hydrophobic membrane that has a configuration that supplies the sample fluid to the microfluidic flow line.

* * * * *